(12) United States Patent
Czech et al.

(10) Patent No.: US 11,519,009 B2
(45) Date of Patent: Dec. 6, 2022

(54) COMPLEXES FOR GENE DELETION AND EDITING

(71) Applicant: UNIVERSITY OF MASSACHUSETTS, Boston, MA (US)

(72) Inventors: Michael P. Czech, Westborough, MA (US); Yuefei Shen, Millbury, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 481 days.

(21) Appl. No.: 16/463,646

(22) PCT Filed: Jan. 8, 2018

(86) PCT No.: PCT/US2018/012764
§ 371 (c)(1),
(2) Date: May 23, 2019

(87) PCT Pub. No.: WO2018/129440
PCT Pub. Date: Jul. 12, 2018

(65) Prior Publication Data
US 2019/0316156 A1 Oct. 17, 2019

Related U.S. Application Data

(60) Provisional application No. 62/443,875, filed on Jan. 9, 2017.

(51) Int. Cl.
*C12N 15/90* (2006.01)
*C12N 15/113* (2010.01)
(Continued)

(52) U.S. Cl.
CPC ........ *C12N 15/907* (2013.01); *A01K 67/0278* (2013.01); *A61K 9/0019* (2013.01);
(Continued)

(58) Field of Classification Search
None
See application file for complete search history.

(56) References Cited

U.S. PATENT DOCUMENTS 4,522,811 A 6/1985 Eppstein et al.
5,990,275 A 11/1999 Whitlow et al.
(Continued)

FOREIGN PATENT DOCUMENTS

WO WO-2014134509 A2 * 9/2014 .......... A61K 36/064
WO WO-2015048577 A2 * 4/2015 .......... A61K 38/465
(Continued)

OTHER PUBLICATIONS

Mokhtarzadeh et al. Aptamers as smart ligands for nano-carriers targeting (TIAC, 2016, 82:316-327) (Year: 2016).*
(Continued)

*Primary Examiner* — Arthur S Leonard
(74) *Attorney, Agent, or Firm* — Lathrop GPM LLP; James H. Velema, Esq.; Michael Spellberg

(57) ABSTRACT

Complexes comprising a nucleic acid-guided endonuclease, a sequence-specific targeting nucleic acid and an amphipathic helical peptide are provided. Compositions and methods for delivery of complexes comprising a nucleic acid-guided endonuclease, a sequence-specific targeting nucleic acid and an amphipathic helical peptide to mammals for both research and therapeutic use are provided. Methods of treating or reducing one or more symptoms of type 2 diabetes, prediabetes and/or gestational diabetes are provided.

15 Claims, 13 Drawing Sheets
Specification includes a Sequence Listing.

(51) Int. Cl.
| | |
|---|---|
| C12N 9/22 | (2006.01) |
| C12N 9/96 | (2006.01) |
| A61K 47/64 | (2017.01) |
| A61K 47/54 | (2017.01) |
| A61P 3/04 | (2006.01) |
| A01K 67/027 | (2006.01) |
| A61K 9/00 | (2006.01) |
| C07K 7/06 | (2006.01) |
| C07K 7/08 | (2006.01) |
| C07K 14/00 | (2006.01) |
| C07K 14/47 | (2006.01) |
| C12N 5/077 | (2010.01) |

(52) U.S. Cl.
CPC ............ *A61K 47/549* (2017.08); *A61K 47/64* (2017.08); *A61P 3/04* (2018.01); *C07K 7/06* (2013.01); *C07K 7/08* (2013.01); *C07K 14/003* (2013.01); *C07K 14/4702* (2013.01); *C12N 5/0653* (2013.01); *C12N 9/22* (2013.01); *C12N 9/96* (2013.01); *C12N 15/113* (2013.01); *A01K 2207/12* (2013.01); *A01K 2217/07* (2013.01); *A01K 2227/105* (2013.01); *A01K 2267/0362* (2013.01)

(56) References Cited

U.S. PATENT DOCUMENTS

| | | | |
|---|---|---|---|
| 6,660,830 | B1 | 12/2003 | Radulescu |
| 7,084,248 | B2 | 8/2006 | Summerton et al. |
| 7,309,576 | B2 | 12/2007 | O'Dowd et al. |
| 8,257,921 | B1 | 9/2012 | Yao et al. |
| 8,580,922 | B2 | 11/2013 | Martini et al. |
| 8,697,359 | B1 | 4/2014 | Zhang et al. |
| 8,828,690 | B2 | 9/2014 | Damude et al. |
| 2005/0261223 | A1* | 11/2005 | Czech ................. A61P 3/10 514/1.2 |
| 2007/0011759 | A1 | 1/2007 | Khan |
| 2010/0093617 | A1 | 4/2010 | Barrangou et al. |
| 2010/0098638 | A1 | 4/2010 | Czech et al. |
| 2010/0192262 | A1 | 7/2010 | Krichevsky |
| 2011/0059502 | A1 | 3/2011 | Chalasani |
| 2012/0042412 | A1 | 2/2012 | Albert et al. |
| 2014/0038281 | A1 | 2/2014 | Langel et al. |
| 2014/0135275 | A1 | 5/2014 | Keefe et al. |
| 2014/0189896 | A1 | 7/2014 | Zhang et al. |
| 2015/0071889 | A1 | 3/2015 | Musunuru et al. |
| 2016/0184449 | A1 | 6/2016 | Czech et al. |
| 2016/0298078 | A1* | 10/2016 | Guay ................. C07K 14/001 |
| 2018/0140717 | A1* | 5/2018 | Furch .................. A61K 47/61 |

FOREIGN PATENT DOCUMENTS

| | | | |
|---|---|---|---|
| WO | WO-2015069587 A2 * | 5/2015 | ............ C07K 19/00 |
| WO | WO 2016/073433 A1 | 5/2016 | |
| WO | WO 2016/161516 A1 | 10/2016 | |

OTHER PUBLICATIONS

Anko et al. (Mar. 2012) "Influence of stearyl and trifluoromethylquinoline modifications of the cell penetrating peptide TP10 on its interaction with a lipid membrane", Biochim. Biophys. Acta (BBA)—Biomembranes, 1818(3):915-924.
Bhaya et al. (2011) "CRISPR—Cas systems in bacteria and archaea: versatile small RNAs for adaptive defense and regulation", Annu. Rev. Genet., 45:273-297.
Chylinski et al. (2013) "The tracrRNA and Cas9 families of type II CRISPR-Cas immunity systems", RNA Biology, 10(5):726-737.
Deltcheva et al. (2011) "CRISPR RNA maturation by trans-encoded small RNA and host factor RNase III", Nature, 471 :602-607.
DiGirolamo et al. (1974) "Metabolic patterns and insulin responsiveness of enlarging fat cells", J. Lipid Res., 15:332-338.
Disse (2013), "Heterogeneity of pregnancy outcomes and risk of LGA neonates in Caucasian females according to IADPSG criteria for gestational diabetes mellitus", Diabetes Metab, 39 (2): 132-138, doi:10.1016/j.diabet.2012.09.006.
Esvelt et al. (2013) "Orthogonal Cas9 proteins for RNA-guided gene regulation and editing", Nature Methods, 10:1116-1121.
Frost et al. (1985) "Evidence for the involvement of vicinal sulfhydryl groups in insulin-activated hexose transport by 3T3-L1 adipocytes", J. Biol. Chem., 260(5):2646-2652.
Gasiunas et al. (2012) "Cas9-crRNA ribonucleoprotein complex mediates specific DNA cleavage for adaptive immunity in bacteria", PNAS U.S.A., 109(39):E2579-E2586.
Hammann et al. (2012) "The ubiquitous hammerhead ribozyme", RNA, 18:871-885.
Heery et al., (1997) "A signature motif in transcriptional co-activators mediates binding to nuclear receptors", Nature, 387(6634):733-736.
Hsu et al. (2014) "Development and Applications of CRISPR-Cas9 for Genome Engineering", Cell 157(6):1262-1278.
Jiang et al. (2013) "CRISPR-assisted editing of bacterial genomes", Nat. Biotech., 31(3):233-239.
Jinek et al. (2012) "A programmable dual-RNA-guided DNA endonuclease in adaptive bacterial immunity", Science, 337(6096):816-821.
Lilley (2011) "Catalysis by the nucleolytic ribozymes", Biochem. Soc. Trans., 39(2):641-646.
Metzger (1998) "Summary and recommendations of the Fourth International Workshop—Conference on Gestational Diabetes Mellitus: the organizing committee", Diabetes Care; 21(Suppl. 2):B161-B167.
Nishimasu et al. (2015) "Crystal Structure of Cas9 in Complex with Guide RNA and Target DNA", Cell, 156(5):935-949.
Pley et al. (1994) "Three-dimensional structure of a hammerhead ribozyme", Nature 372:68-74.
Regberg et al. (2014) "Rational design of a series of novel amphipathic cellpenetrating peptides", Int. J. Pharm.464:111-116.
Sapranauskas et al. (2011) "The *Streptococcus thermophilus* CRISPR/Cas system provides immunity in *Escherichia coli*", Nucleic Acids Res., 39(21):9275-9282.
Scott et al. (1995) "The crystal structure of an all-RNA hammerhead ribozyme: a proposed mechanism for RNA catalytic cleavage", Cell 81(7):991-1002.
Shah et al. (2013) "Protospacer recognition motifs: mixed identities and functional diversity", RNA Biology, 10(5):891-899.
Sternberg et al. (2014) "DNA interrogation by the CRISPR RNA-guided endonuclease Cas9", Nature, 507(7490):62-67.
Summerton (2005) "Endo-Porter: a novel reagent for safe, effective delivery of substances into cells", Ann. N Y Acad. Sci,. 1058:62-75.
Tesz et al. (2011) "Glucan particles for selective delivery of siRNA to phagocytic cells in mice", Biochem. J., 436(2):351-362.
Tiraby et al. (2003) "Acquirement of brown fat cell features by human white adipocytes", J. Biol. Chem., 278(35):33370-33376.
Zetsche et al. (2015) "Cpf1 is a single RNA-guided endonuclease of a class 2 CRISPR-Cas system", Cell 163(3)759-771.
Doench et al., "Optimized sgRNA design to maximize activity and minimize off-target effects of CRISPR-Cas9", Nat Biotech, 34: 184-191, Feb. 2016.
International Search Report and Written Opinion in related PCT Application No. PCT/US2018/012764, dated Apr. 30, 2018 (23 pages).
Puri et al., "RNAi-based gene silencing in primary mouse and human adipose tissues", Journal of Lipid Research, 48: 465-72, 2007.
Steel et al., "Role of the RIP140 corepressor in ovulation and adipose biology", Journal of Endocrinology, 185: 1-9, 2005.

* cited by examiner

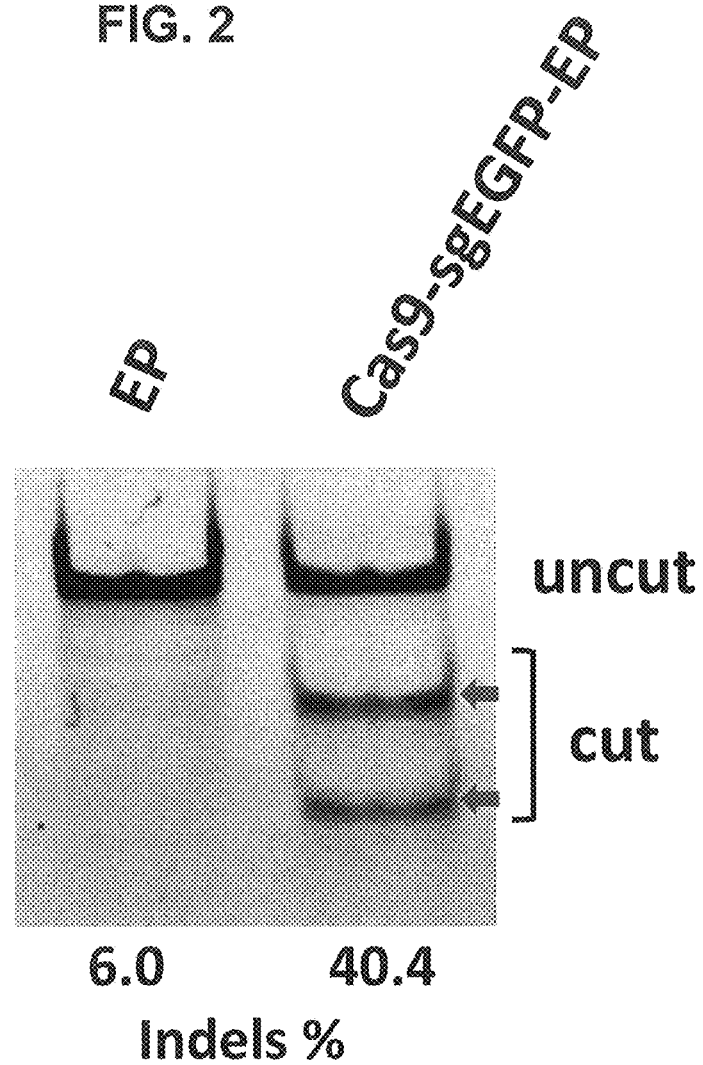

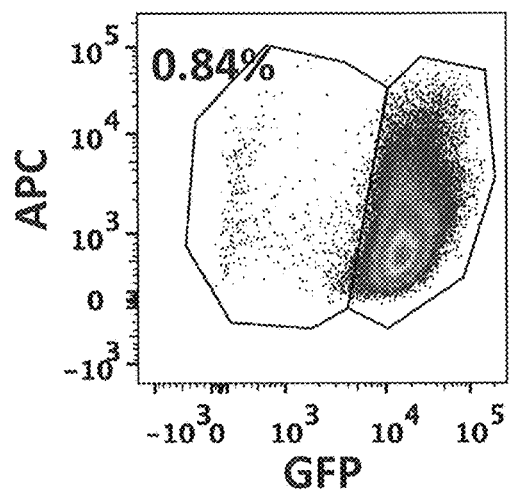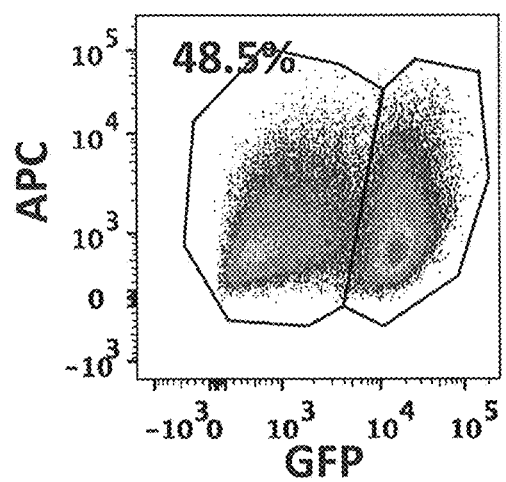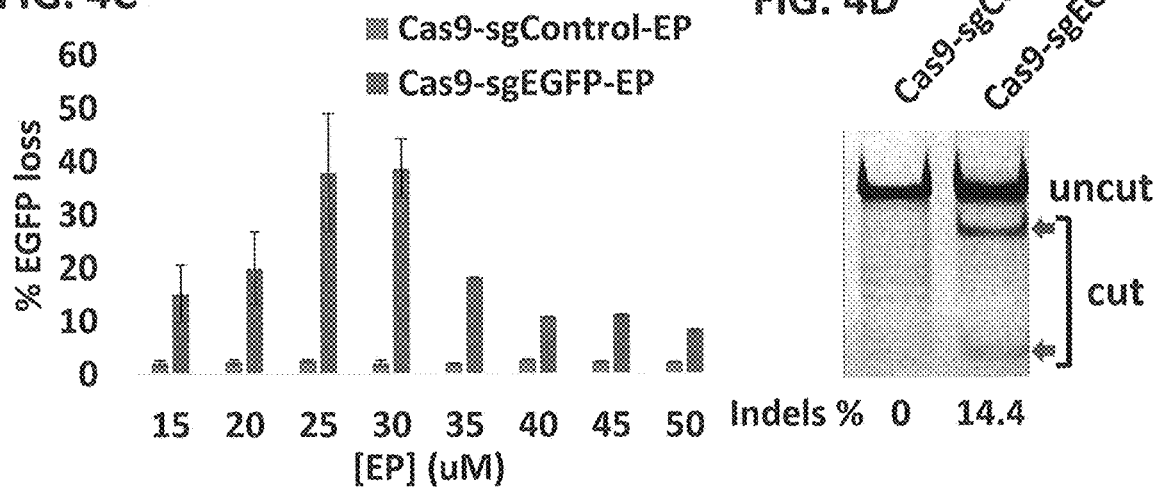

FIG. 6A
sgRNA targeting RIP140 sequence #3 (sgRIP140-3):
GGAGTCGAAGAACATCTGCATGG (SEQ ID NO: 33)
FIG. 6B
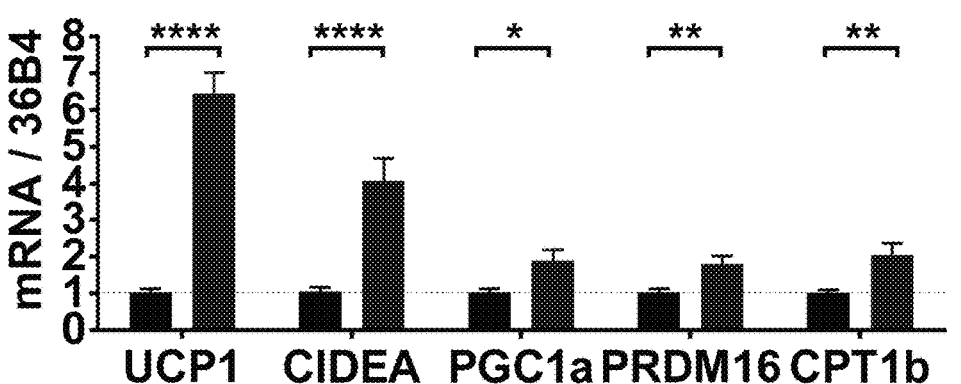
FIG. 6C
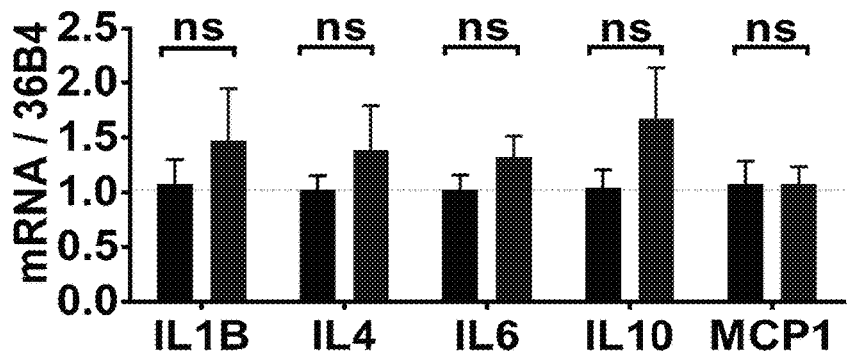
FIG. 6D
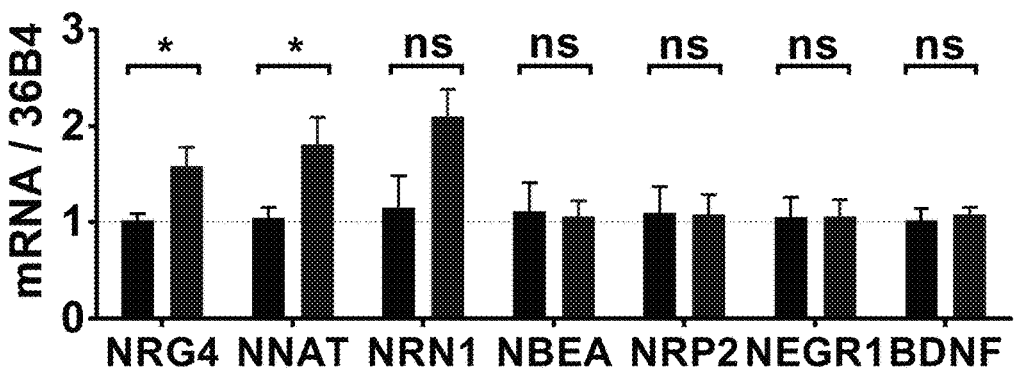

sgRIP140-3
On-Target    GGAGTCGAAGAACATCTGCATGG (SEQ ID NO: 33)
Off-Target 1  GGACTATAAGAACATCTGCATGG (SEQ ID NO: 35)
Off-Target 2  GGAGATGAAGAACATGTGCATGG (SEQ ID NO: 36)
Off-Target 3  GGAGAAGAAGAACCTCTGCATGG (SEQ ID NO: 37)

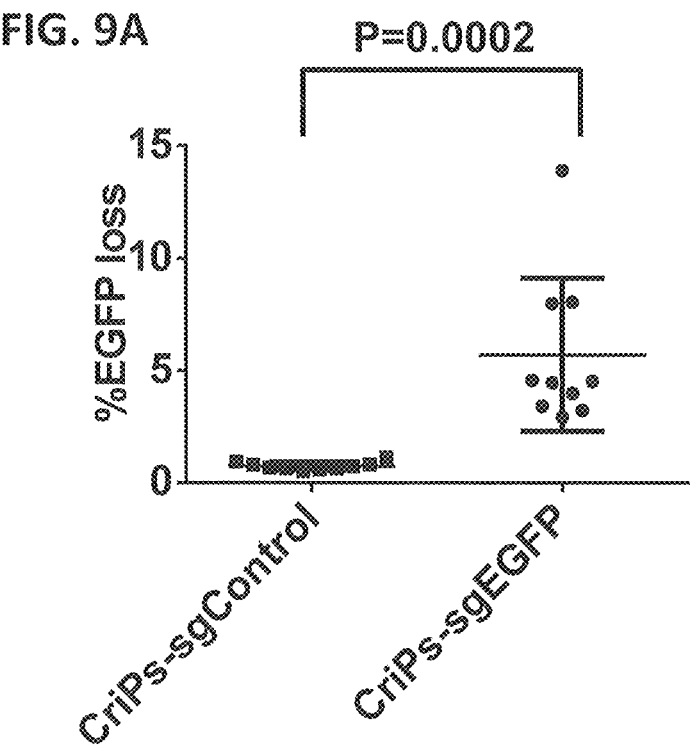
FIG. 9A
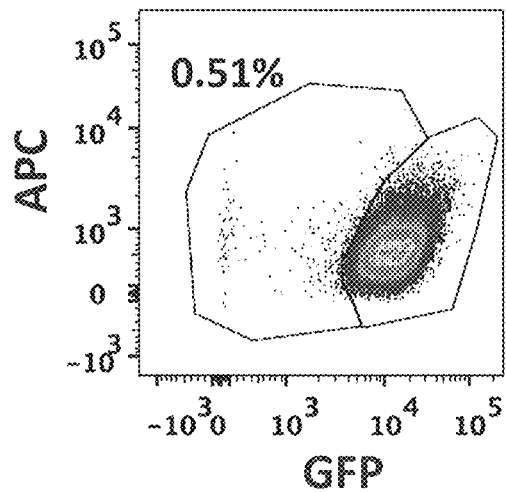
FIG. 9B  CriPs-sgControl
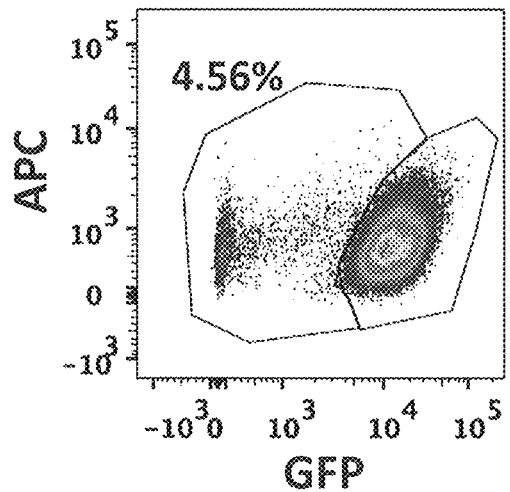
FIG. 9C  CriPs-sgEGFP

FIG. 10

```
                              ▼
GGTGAGCAAGGGCGAGGAGCTGTTC..ACCGGGGTGGTGCCCATCCT   WT   (SEQ ID NO: 38)
GGTGAGCAAGGGCGAGGAGCTGTTCA.ACCGGGGTGGTGCCCATCCT   +1   (SEQ ID NO: 39)
GGTGAGCAAGGGCGAca..........CCGGGGTGGTGCCCATCCT   S2-9 (SEQ ID NO: 40)
GGTGAGCAAGGGCGAG............CGGGGTGGTGCCCATCCT   -11  (SEQ ID NO: 41)
GGTGAGCAAGGGCGAGGAGCT........GGGGTGGTGCCCATCCT   -7   (SEQ ID NO: 42)
GGTGAGCAAGGGCGAGGAGC.........CGGGGTGGTGCCCATCCT   -7   (SEQ ID NO: 43)
GGTGAGCAAGGGCGAGGAGCTG.....ACCGGGGTGGTGCCCATCCT   -3   (SEQ ID NO: 44)
GGTGAGCAAGGGCGAGGAGCTGTT...ACCGGGGTGGTGCCCATCCT   -1   (SEQ ID NO: 45)
GGTGAGCAAGGGCGAGGAGCTGTT....CCGGGGTGGTGCCCATCCT   -2   (SEQ ID NO: 46)
GGTGAGCAAGGGCGAGGAGCT......ACCGGGGTGGTGCCCATCCT   -4   (SEQ ID NO: 47)
GGTGAGCAAGGGCGAGGAGCTGTT......GGGGTGGTGCCCATCCT   -4   (SEQ ID NO: 48)
GGTGAGCAAGGGCGAGGAGC..............TGGTGCCCATCCT  -12  (SEQ ID NO: 49)
```

COMPLEXES FOR GENE DELETION AND EDITING

RELATED APPLICATIONS

This application is a 35 U.S.C. § 371 filing of International Patent No. PCT/US2018/012764, filed Jan. 8, 2018, which claims priority to U.S. Provisional Patent Application Ser. No. 62/443,875, filed Jan. 9, 2017, which are hereby incorporated herein by reference in their entirety for all purposes.

STATEMENT OF FEDERALLY SPONSORED RESEARCH

This invention was made with government support under Grant No. DK010347 awarded by the National Institutes of Health. The Government has certain rights in this invention.

TECHNICAL FIELD

The present disclosure relates to nucleic acid-guided endonuclease-sequence-specific targeting nucleic acid-amphipathic peptide complexes (e.g., Cas9-gRNA-Endo-Porter complexes) that target a gene (e.g., RIP140) for editing and/or deletion. The complexes described herein are useful for delivery of CRISPR/Cas9 materials to mammals for research as well as therapeutic applications. Additionally, the present disclosure relates to a method of treatment of type 2 diabetes, prediabetes and/or gestational diabetes by administering one or more complexes disclosed herein to a subject in need thereof.

BACKGROUND

RNA-guided engineered endonucleases (RGENs) derived from the prokaryotic adaptive immune system known as clustered regularly interspaced short palindromic repeats (CRISPR) involves two major components: a nuclease (e.g., Cas9) and a sequence-specific targeting nucleic acid (e.g., a small guide RNA). RGENs can mediate gene deletion and/or editing. The CRISPR-Cas9 system represents a promising platform for genome editing that is most often delivered in vivo and in vitro through a plasmid-based system. The success of the CRISPR-Cas9 system is often limited by uncontrolled integration of DNA segments into the host genome, unwanted immune response to the plasmids encoding Cas9 protein and/or guide RNA, and unintended off-target effects of Cas9 itself.

Recently, CRISPR-Cas9 technology has generated a lot of interest for use as a therapeutic. However, delivery of CRISPR technology to mammals in vivo presents a significant challenge to the use of CRISPR as a therapeutic. Direct delivery of Cas9 protein and guide RNA could circumvent the safety problems associated with plasmid delivery and therefore represents an attractive tool for genome engineering. There is clearly a need for technology that efficiently delivers CRISPR-Cas9 components in mammals, especially for potential use in disease areas with major unmet needs.

Many recent advances in CRISPR have addressed the off-target issue that has been known as a major hurdle of translating CRISPR-Cas9 technology to therapeutics. Multiple versions of Cas9 have been generated to increase the specificity of CRISPR-Cas9 genome editing such as a mutation in Cas9 that causes single strand nicks instead of double strand breaks (Cas9-nickase, Cas9-n), Cas9 fused to the non-specific endonuclease FokI (Cas9-FokI) which requires dimerization to cleave target DNA, and a mutation in Cas9 that dampens the ability of Cas9 to cleave off target sites in DNA essentially leading to a more efficient Cas9 (enhanced Cas9, eSpCas9 or high fidelity Cas9, SpCas9-HF1). Despite the multitude of advances in CRISPR-Cas9 specificity there is a lack of technologies to improve the in vivo delivery of plasmid-free CRISPR-Cas9 components, which is of high priority in order to further the therapeutic potential of the CRISPR-Cas9 system.

Type 2 diabetes therapeutics represent a major unmet need for a significant amount of the US population. Obesity has increased worldwide and the problem is particularly acute in the US. Overweight and obese men and women account for about two-thirds of the US population, and are greatly at risk to develop type 2 diabetes. Alarmingly, according to the Center for Disease Control (CDC), African Americans have an incidence of type 2 diabetes that is much higher than the general population and all Americans over the age of 65 have an incidence of type 2 diabetes of over 25%. These remarkable statistics are particularly worrisome when one considers the co-morbidities of type 2 diabetes, which include about a two-fold increase in the incidence of cardiovascular disease, and almost 700,000 cases of advanced retinopathy with danger of severe vision loss. Kidney failure is also a major problem, with almost 250,000 diabetics currently on chronic dialysis or with a kidney transplant. Neuropathy, periodontal disease and non-alcoholic fatty liver disease are also frequent syndromes associated with type 2 diabetes. Thus, this disease is a major threat to the US population. Importantly, these co-morbidities are almost all directly linked to the ability of patients to control blood glucose levels, and reducing blood glucose concentrations towards normal has a huge beneficial effect to limit these associated maladies. Advancing a therapeutic solution to increase glucose tolerance would likely alleviate many of the maladies associated with type 2 diabetes in the US population.

White adipose tissue (WAT) depots that store triglycerides are distributed throughout the body and expand greatly during the onset of obesity. Expansion of the visceral depots of WAT are particularly well correlated with metabolic disease, insulin resistance and development of type 2 diabetes, which occurs when the beta cells of the pancreas are unable to produce enough insulin to overcome insulin resistance and maintain normal fasting levels of glucose. It is still contested exactly how unhealthy expansion of WAT leads to glucose intolerance, but a major hypothesis is that lipids that cannot be stored in maximally expanded WAT are ectopically deposited in other tissues, causing insulin resistance. Importantly, it was discovered that humans have another type of adipose tissue, denoted as brown adipose tissue (BAT), containing brown adipocytes that are loaded with mitochondria that can be uncoupled by uncoupling protein UCP-1 to produce heat. Thus BAT is a fat burning tissue in response to catecholamine, as opposed to the fat storing WAT. Furthermore, WAT was found to contain some adipocytes that resemble brown adipocytes and are greatly increased in WAT in response to cold exposure (through catecholamine stimulation). These cells that arise in WAT when humans or mice are cold exposed also express UCP-1 (denoted as "beige" adipocytes) and show high fatty acid oxidation rates.

Type 2 diabetes, along with a multitude of other diseases, could greatly benefit from CRISPR-based therapeutics.

Therefore, it is of great importance to develop a system that improves the efficiency of CRISPR-Cas9 in vivo.

SUMMARY

The present disclosure is based on the discovery of nucleic acid-guided endonuclease-sequence-specific targeting nucleic acid-amphipathic peptide complexes (e.g., Cas9-gRNA-Endo-Porter complexes) that target a gene (e.g., the RIP140 gene) for editing and/or deletion. In one aspect, the present disclosure provides a composition comprising a nucleic acid-guided endonuclease, a sequence specific targeted nucleic acid, and an amphipathic helical peptide. In some embodiments the nucleic acid-guided endonuclease, sequence specific targeted nucleic acid, and amphipathic helical peptide form a complex wherein the amphipathic helical peptide mediates delivery of the complex to a target cell, and wherein the nucleic acid-guided endonuclease mediates editing or deletion of a target gene in the target cell.

In certain embodiments, the amphipathic peptide is selected from the group consisting of: H2N-LHHLLHHLLHHLHHLLHHLHHLLHHL (SEQ ID NO: 5)-COOH; H2N-LHKLLHHLLHHLHKLLHHLHKL (SEQ ID NO: 6)-COOH; H2N-LHKLLHHLLHKLHHLLHKLHHLLHHL (SEQ ID NO: 7)-COOH; H2N-LHHLLHHLLHHLHHL (SEQ ID NO: 8)-COOH; H2N-HHLLHHLHHLLHHL (SEQ ID NO: 9)-COOH; H2N-LHLLHHLLHHLHHL (SEQ ID NO: 10)-COOH; H2N-LHHLLHLLHHLLHHL (SEQ ID NO: 11)-COOH; H2N-LHKLLHHLLHHLHK (SEQ ID NO: 12)-COOH; H2N-LHKLLHHLHHLLHKL (SEQ ID NO: 13)-COOH; H2N-KLHHLLHKLHHLLHH (SEQ ID NO: 14)-COOH; H2N-HLHLLHHLLHH (SEQ ID NO: 15)-COOH; H2N-LHLLHHLLHH (SEQ ID NO: 16)-COOH; H2N-LHKLLHHLLHKLHHL (SEQ ID NO: 17)-COOH; H2N-LHLLHH (SEQ ID NO: 18)-COOH; H2N-LHHLL (SEQ ID NO: 19)-COOH; H2N-LHKLL (SEQ ID NO: 20)-COOH and Endo-Porter. In other embodiments, the amphipathic helical peptide is Endo-Porter.

In certain embodiments, the nucleic acid-guided endonuclease is Cas9. In some embodiments the Cas9 is an *E. coli* Cas9, a *Streptococcus pyogenes* Cas9 or a *Staphylococcus aureus* Cas9.

In certain embodiments, the sequence specific nucleic acid is a guide RNA. In some embodiments, the guide RNA is between 15 and 30 bases in length, and comprises a region which is at least 90% homologous to GGTTTGGAGTCACGTCAGGG (SEQ ID NO: 1), GGATTTAAGGTGCTATGGCG (SEQ ID NO: 2), GGAGTCGAAGAACATCTGCA (SEQ ID NO: 3) or GGAGTACTGCAGGCATACGG (SEQ ID NO: 4). In other embodiments, the guide RNA comprises a region that is at least 95% homologous to SEQ ID NO: 1, SEQ ID NO: 2, SEQ ID NO: 3 or SEQ ID NO: 4. In other embodiments, the guide RNA comprises SEQ ID NO: 1, SEQ ID NO: 2, SEQ ID NO: 3 or SEQ ID NO: 4. In other embodiments, the guide RNA comprises SEQ ID NO: 3.

In certain embodiments, the target gene is RIP140. In other embodiments, the target cell is mammalian. In further embodiments the mammalian target cell is an adipocyte or pre-adipocyte.

In other embodiments, the complex further comprises an aptamer molecule with binding specificity for the target cell. In some embodiments, the aptamer forms a non-covalent binding interaction with the amphipathic helical peptide. In other embodiments, the aptamer is conjugated to the amphipathic helical peptide.

In further embodiments, the complex is encapsulated in a glucan particle (GP).

In another aspect, the present disclosure provides methods of editing or deleting a target gene in a cell comprising contacting a cell with a complex comprising a nucleic acid-guided endonuclease, a sequence-specific targeting nucleic acid and an amphipathic helical peptide and allowing the complex to enter the cell and edit or delete the target gene.

In certain embodiments, the amphipathic peptide is selected from the group consisting of: H2N-LHHLLHHLLHHLHHLLHHLHHLLHHL (SEQ ID NO: 5)-COOH; H2N-LHKLLHHLLHHLHKLLHHLH-HLLHKL (SEQ ID NO: 6)-COOH; H2N-LHKLLHHLLHKLHHLLHKLHHLLHHL (SEQ ID NO: 7)-COOH; H2N-LHHLLHHLLHHLHHL (SEQ ID NO: 8)-COOH; H2N-HHLLHHLHHLLHHL (SEQ ID NO: 9)-COOH; H2N-LHLLHHLLHHLHHL (SEQ ID NO: 10)-COOH; H2N-LHHLLHLLHHLLHHL (SEQ ID NO: 11)-COOH; H2N-LHKLLHHLLHHLHK (SEQ ID NO: 12)-COOH; H2N-LHKLLHHLHHLLHKL (SEQ ID NO: 13)-COOH; H2N-KLHHLLHKLHHLLHH (SEQ ID NO: 14)-COOH; H2N-HLHLLHHLLHH (SEQ ID NO: 15)-COOH; H2N-LHLLHHLLHH (SEQ ID NO: 16)-COOH; H2N-LHKLLHHLLHKLHHL (SEQ ID NO: 17)-COOH; H2N-LHLLHH (SEQ ID NO: 18)-COOH; H2N-LHHLL (SEQ ID NO: 19)-COOH; H2N-LHKLL (SEQ ID NO: 20)-COOH and Endo-Porter. In other embodiments, the amphipathic helical peptide is Endo-Porter.

In some embodiments, the target gene is RIP140. In other embodiments, the sequence specific targeting nucleic acid is a guide RNA. In further embodiments, the cell is an adipocyte or pre-adipocyte. In some embodiments, the guide RNA comprises a region that is at least 90% homologous to SEQ ID NO: 1, SEQ ID NO: 2, SEQ ID NO: 3 or SEQ ID NO: 4. In further embodiments, the guide RNA comprises a region that is at least 95% homologous to SEQ ID NO: 1, SEQ ID NO: 2, SEQ ID NO: 3 or SEQ ID NO: 4. In further embodiments, the guide RNA comprises SEQ ID NO: 1, SEQ ID NO: 2, SEQ ID NO: 3 or SEQ ID NO: 4. In other embodiments, the guide RNA comprises SEQ ID NO: 3.

In other embodiments, the nucleic acid-guided endonuclease is Cas9.

In some embodiments, the complex further comprises an aptamer molecule with binding specificity for the target cell. In other embodiments, the aptamer forms a non-covalent binding interaction with the amphipathic helical peptide. In further embodiments, wherein the aptamer is conjugated to the amphipathic helical peptide.

In other embodiments, the complex is encapsulated in a glucan particle (GP).

In yet other aspects, the present disclosure provides methods of improving glucose tolerance in a subject, comprising administering to the subject a therapeutically effective amount of a pharmaceutical composition comprising a complex including a nucleic acid-guided endonuclease, a sequence-specific targeting nucleic acid and an amphipathic helical peptide, wherein the complex edits or deletes a target gene in the subject. In some embodiments, the subject is at risk for or suffering from a disorder related to glucose metabolism. In some embodiments, the disorder is type 2 diabetes, prediabetes or gestational diabetes. In some embodiments, the method results in one or more of a decrease in white fat levels, an increase in brown fat levels and an increase in beige fat levels. In further embodiments, the methods result in increased fatty acid oxidation in the subject.

In certain embodiments, the amphipathic peptide is selected from the group consisting of: H2N-LHHLLHHLLHHLHHLLHHLHHLLHHL (SEQ ID NO: 5)-COOH; H2N-LHKLLHHLLHHLHKLLHHLH-HLLHKL (SEQ ID NO: 6)-COOH; H2N-LHKLLHHLLHKLHHLLHKLHHLLHHL (SEQ ID NO: 7)-COOH; H2N-LHHLLHHLLHHLHHL (SEQ ID NO: 8)-COOH; H2N-HHLLHHLHHLLHHL (SEQ ID NO: 9)-COOH; H2N-LHLLHHLLHHLHHL (SEQ ID NO: 10)-COOH; H2N-LHHLLHLLHHLLHHL (SEQ ID NO: 11)-COOH; H2N-LHKLLHHLLHHLHK (SEQ ID NO: 12)-COOH; H2N-LHKLLHHLHHLLHKL (SEQ ID NO: 13)-COOH; H2N-KLHHLLHKLHHLLHH (SEQ ID NO: 14)-COOH; H2N-HLHLLHHLLHH (SEQ ID NO: 15)-COOH; H2N-LHLLHHLLHH (SEQ ID NO: 16)-COOH; H2N-LHKLLHHLLHKLHHL (SEQ ID NO: 17)-COOH; H2N-LHLLHH (SEQ ID NO: 18)-COOH; H2N-LHHLL (SEQ ID NO: 19)-COOH; H2N-LHKLL (SEQ ID NO: 20)-COOH and Endo-Porter. In other embodiments, the amphipathic helical peptide is Endo-Porter.

In some embodiments, the sequence-specific targeting nucleic acid is a guide RNA. In other embodiments, the target gene is RIP140. In further embodiments, the RIP140 gene is inactivated or deleted.

In some embodiments, the nucleic acid-guided endonuclease is Cas9.

In some embodiments, the complex further comprises an aptamer molecule with binding specificity for the target cell. In other embodiments, the aptamer forms a non-covalent binding interaction with the amphipathic helical peptide. In further embodiments, the aptamer is conjugated to the amphipathic helical peptide.

In some embodiments, the complex is encapsulated in a glucan particle (GP).

In a further aspect, the present disclosure provides methods of improving glucose tolerance in a subject, comprising contacting an adipocyte cell or pre-adipocyte cell ex vivo with a complex including a Cas9, a RIP140 guide RNA and an amphipathic helical peptide for a sufficient amount of time to delete or inactivate RIP140 gene in the cell, and implanting into the subject the cell having the deleted or inactivated RIP140 gene.

In certain embodiments, the amphipathic peptide is selected from the group consisting of: H2N-LHHLLHHLLHHLHHLLHHLHHLLHHL (SEQ ID NO: 5)-COOH; H2N-LHKLLHHLLHHLHKLLHHLH-HLLHKL (SEQ ID NO: 6)-COOH; H2N-LHKLLHHLLHKLHHLLHKLHHLLHHL (SEQ ID NO: 7)-COOH; H2N-LHHLLHHLLHHLHHL (SEQ ID NO: 8)-COOH; H2N-HHLLHHLHHLLHHL (SEQ ID NO: 9)-COOH; H2N-LHLLHHLLHHLHHL (SEQ ID NO: 10)-COOH; H2N-LHHLLHLLHHLLHHL (SEQ ID NO: 11)-COOH; H2N-LHKLLHHLLHHLHK (SEQ ID NO: 12)-COOH; H2N-LHKLLHHLHHLLHKL (SEQ ID NO: 13)-COOH; H2N-KLHHLLHKLHHLLHH (SEQ ID NO: 14)-COOH; H2N-HLHLLHHLLHH (SEQ ID NO: 15)-COOH; H2N-LHLLHHLLHH (SEQ ID NO: 16)-COOH; H2N-LHKLLHHLLHKLHHL (SEQ ID NO: 17)-COOH; H2N-LHLLHH (SEQ ID NO: 18)-COOH; H2N-LHHLL (SEQ ID NO: 19)-COOH; H2N-LHKLL (SEQ ID NO: 20)-COOH and Endo-Porter. In other embodiments, the amphipathic helical peptide is Endo-Porter.

In some embodiments, the subject is a mouse. In further embodiments, the mouse is humanized.

In other aspects, the present disclosure provides a guide RNA of between 15 and 30 bases in length, that comprises a region which is at least 95% homologous to SEQ ID NO: 1.

In certain embodiments, the guide RNA comprises a region that is at least 98% homologous to SEQ ID NO: 1. In other embodiments, the guide RNA comprises SEQ ID NO: 1.

In other aspects, the present disclosure provides a guide RNA comprising SEQ ID NO: 1.

In other aspects, the present disclosure provides a guide RNA of between 15 and 30 bases in length, that comprises a region which is at least 95% homologous to SEQ ID NO: 2.

In certain embodiments, the guide RNA comprises a region that is at least 98% homologous to SEQ ID NO: 2. In other embodiments, the guide RNA comprises SEQ ID NO: 2.

In other aspects, the present disclosure provides a guide RNA comprising SEQ ID NO: 2.

In other aspects, the present disclosure provides a guide RNA of between 15 and 30 bases in length, that comprises a region which is at least 95% homologous to SEQ ID NO: 3.

In certain embodiments, the guide RNA comprises a region that is at least 98% homologous to SEQ ID NO: 3. In other embodiments, the guide RNA comprises SEQ ID NO: 3.

In other aspects, the present disclosure provides a guide RNA comprising SEQ ID NO: 3.

In other aspects, the present disclosure provides a guide RNA of between 15 and 30 bases in length, that comprises a region which is at least 95% homologous to SEQ ID NO: 4.

In certain embodiments, the guide RNA comprises a region that is at least 98% homologous to SEQ ID NO: 4. In other embodiments, the guide RNA comprises SEQ ID NO: 4.

In other aspects, the present disclosure provides a guide RNA comprising SEQ ID NO: 4.

The summary of the disclosure described above is non-limiting and other features and advantages of the disclosed apparatus and methods will be apparent from the following drawings, detailed description of the disclosure, and claims.

BRIEF DESCRIPTION OF THE DRAWINGS

FIG. 2 shows that EGFP deletion was achieved in EGFP expressing J774A.1 cells following treatment with sgEGFP- CriPs. EGFP-J774 cells were treated with CriPs with sgRNA sequence targeting EGFP (sgEGFP) or a control sequence (sgControl). Gene editing was detected in the EGFP genomic DNA following treatment with CriPs. Insertions and deletions (indels) in the GFP genomic locus were measured by T7E1 assay. Uncut GFP DNA: 292 bp, Cut GFP DNA: 179 bp+113 bp.

FIG. 3A shows J774A.1 cells with no treatment. FIG. 3B shows J774A.1 cells treated with sgCONTROL-CriPs. FIG. 3C J774A.1 cells treated with Cas9-sgEGFP. FIG. 4D shows J774A.1 cells treated with CriPs targeting EGFP (Cas9-sgEGFP-EP). FIG. 3E shows a dose response of Cas9-sgEGFP (1:1) with 2 µM of EP. Cas9: 150 nM, sgEGFP: 150 nM, EP: 2 µM.

FIG. 4A-FIG. 4D show FACS analysis results demonstrating that GFP deletion can be achieved in GFP expressing primary pre-adipocytes by treatment with CriPs targeting GFP. Primary GFP expressing pre-adipocytes were isolated from GFP transgenic mice and seeded in 12 well plates with $8\times10^4$ cells per well overnight. Cells were treated with CriPs complexes with gRNA sequence targeting GFP (sgGFP) or a control sequence (sgCONTROL). After 24 hours, CriPs were replaced by fresh culture media. At day 5, FACS analysis was performed to measure the loss of GFP. 7-AAD staining was used to determine live cells and dead cells. % GFP-shift and % GFP+ was calculated from the live cells. T7E1 assay was also performed to determine the indels in the EGFP genomic DNA. FIG. 4A shows cells treated with CriPs/sgGFP. FIG. 4B shows cells treated with CriPs/sgCONTROL. FIG. 4C shows cells treated with Cas9/sgRNA complexes coated with increasing concentrations of EP. FIG. 4D shows indels % measurements by T7E1 assay in GFP genomic DNA isolated from primary GFP pre-adipocytes. Uncut GFP DNA: 401 bp, Cut GFP DNA: 288 bp+113 bp.

FIG. 5A shows that gene editing was detected in the RIP140 genomic DNA treated with CriPs using the T7E1 assay. FIG. 5B shows UCP1 expression was measured by quantitative RT-PCR. F.C. is fold-change.

FIG. 6A-FIG. 6D show that treatment with Cas9-sgRIP140-3 CriPs altered expression of thermogenic genes. FIG. 6A shows sgRNA targeting RIP140 sequence #3 (sgRIP140-3). TGG is the PAM site. With the treatment of Cas9-sgRIP140-3-EP and Cas9-sgControl-EP, gene expression was measured by RT-PCR. FIG. 6B shows thermogenic genes, FIG. 6C shows inflammatory genes, and FIG. 6D shows neurotropic factors.

FIG. 7A depicts off-target effects of Cas9-sgRIP140-3 were determined by T7E1 assay. Expected DNA bands cleaved by T7E1: On-target: 420 bp=270 bp+150 bp; Off-target 1: 386 bp=283 bp+103 bp; Off-target 2: 387 bp=229 bp+158 bp; Off-target 3: 352 bp=182 bp+172 bp. FIG. 7B depicts mismatched bases that are underlined and in bold. PAM is in bold.

FIG. 9A-FIG. 9C show that CriPs treatment in vivo resulted in decreased GFP expression in GFP transgenic mice C57BL6-Tg(UBC-GFP). UBC-GFP mice (female, 8 weeks old) were intraperitoneally injected once a day for 5 days with CriPs targeting GFP (sgGFP) or CriPs without gRNA. On day 6, mice were sacrificed and the peritoneal cavities were washed with 5 mL of ice-cold PBS to isolate peritoneal exudate cells (PECs). The cells were plated in media (DMEM supplemented with 10% (v/v) FBS, 100 µg/mL streptomycin and 100 units/mL penicillin) overnight to enrich for macrophages. At day 10 (5 days after the last injection), adherent cells were collected. FACS analysis was performed to measure the loss of GFP. 7-AAD staining was used to determine live cells and dead cells. % GFPshift and % GFP+ were calculated from the live cells. FIG. 9A shows quantification of flow cytometry data showing EGFP loss in mice injected with CriPs with sgEGFP or with a control sequence (sgControl). 3-8 week old EGFP male C57BL/6 mice, n=10. FIG. 9B depicts representative flow cytometry data of one GFP mouse treated with CriPs-sgControl. FIG. 9C depicts representative flow cytometry data of one GFP mouse treated with CriPs-sgEGFP.

FIG. 10 shows indels detected in the GFP genomic locus by in vivo intraperitoneal injections (i.p.) of CriPs-sgGFP in GFP mice measured by deep sequencing. DNA sequences of the GFP wild-type (WT) and mutants are shown. The PAM site is underlined. The cleavage site is indicated by an arrowhead. The column on the right indicates the number of inserted (+) or deleted (−) bases or SNPs (S).

DETAILED DESCRIPTION OF THE DISCLOSURE

Figure 1:
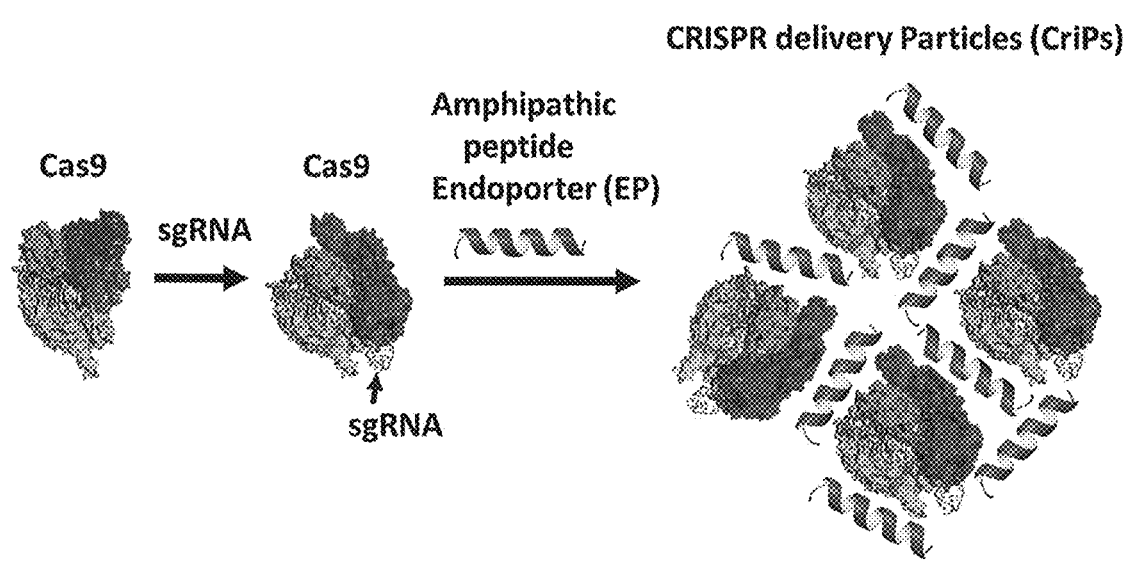
FIG. 1 shows the preparation CRISPR-based nanoparticles (CriPs) (i.e., nucleic acid-guided endonuclease-sequence-specific targeting nucleic acid-amphipathic peptide complexes (e.g., Cas9-gRNA-Endo-Porter complexes)) for gene editing in adipose tissues. Purified bacterial Cas9 protein that was carefully processed to remove endotoxin and other contaminants was used for loading of gRNA. The gRNA sequence was designed to target a selected gene at a site adjacent to a PAM sequence in the DNA of that target gene. The loaded Cas9/sgRNA complexes were then coated with an amphipathic peptide, denoted as Endo-Porter. The Endo-Porter peptide coating on the CriPs was required to mediate uptake of the Cas9/sgRNA complexes into live cells without toxicity or detectable damage.
Figure 3A:
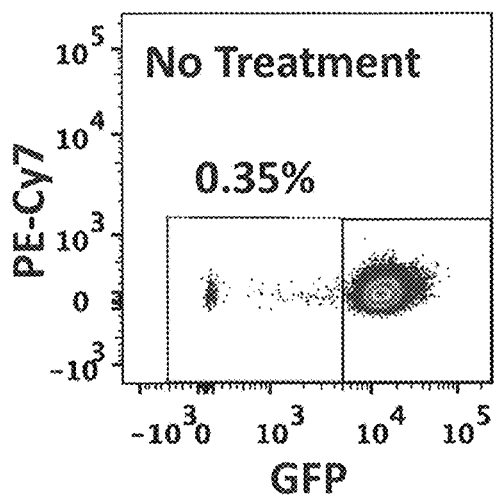
FIG. 3A-FIG. 3E show that efficient genome editing was achieved by the treatment of CriPs in the EGFP expressing macrophage cell line (J774A.1 cells). GFP expressing J774A.1 cells were plated in 12 well plates with $1*10^5$ cells per well overnight. Cells were treated with CriPs—EP coated Cas9/sgRNA complexes with sgRNA sequence targeting GFP (sgGFP) or a control sequence (sgCONTROL). 24 hours later, CriPs were replaced with fresh culture media. At day 5 post treatment, FACS analysis was performed to measure the loss of GFP. 7-AAD staining was used to determine live cells and dead cells. % GFP-shift and % GFP+ was calculated from the live cells.
Figure 3B:
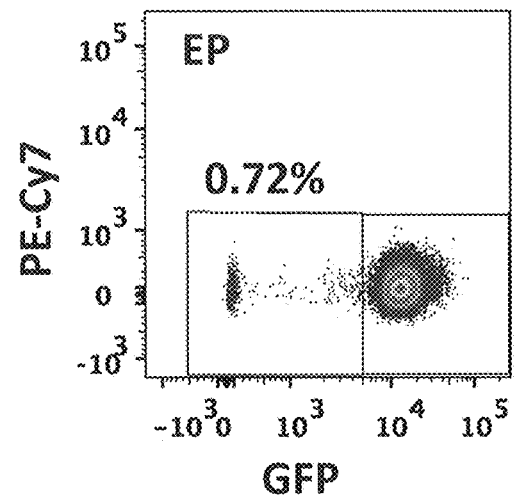
Figure 3C:
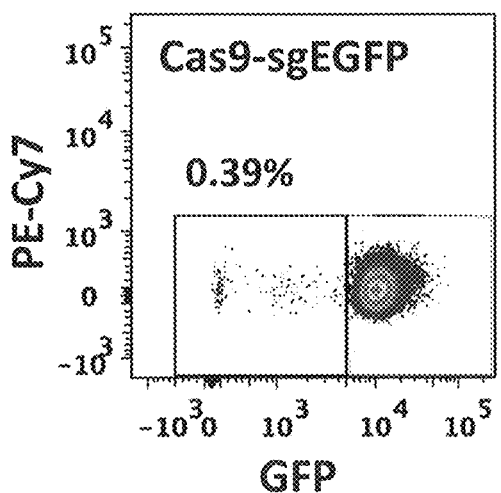
Figure 3D:
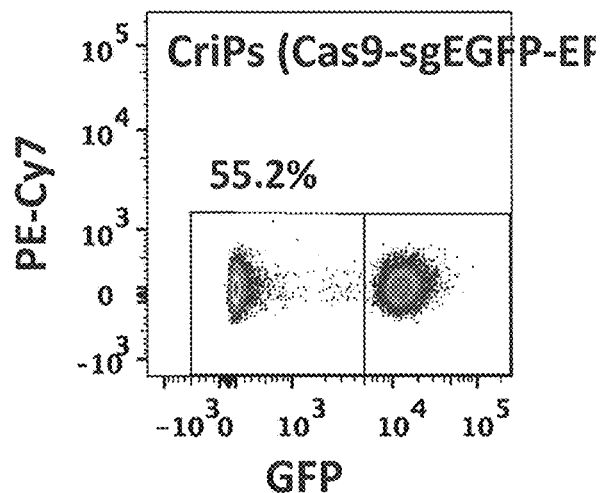
Figure 3E:
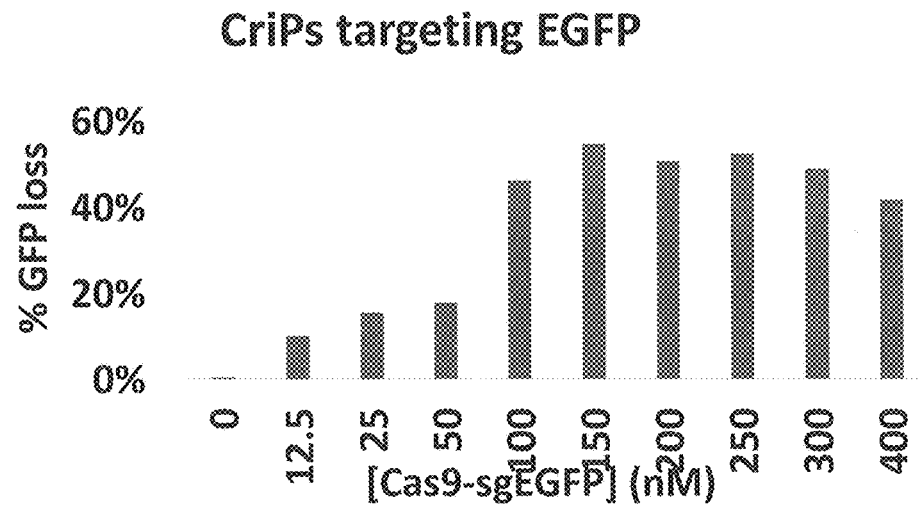

The present disclosure is directed to a novel complex designed to deliver CRISPR-Cas9 components efficiently in mammals.

The present disclosure is also directed to a novel method of treatment in a subject with type 2 diabetes by administering a therapeutic amount of a complex comprising an RNA directed nuclease, a sequence specific nucleic acid, and an amphipathic peptide in order to increase glucose tolerance in the subject.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting. As used herein, unless otherwise stated, the singular forms "a," "an," and "the" include plural reference. Thus, for example, a reference to "a protein" includes a plurality of protein molecules.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

As used herein, the term "RNA-guided endonuclease" refers to a protein that can be produced in and purified from bacteria (or can be recombinantly produced) having double-stranded DNA cleaving activity which is guided to a specific target site in the genome by a guide RNA (gRNA). In some embodiments, the RNA-guided endonuclease is Cas9 or a variant of Cas9. In certain embodiments, a Cas9 variant can contain a genetic mutation that causes Cas9 to function as a nickase, in which the Cas9 nickase will cleave only one strand of DNA (Cas9-nickase, Cas9-n). In other embodiments, a Cas9 variant can contain a genetic mutation that causes Cas9 to have less off target activity (enhanced Cas9, eSpCas9 or high-fidelity Cas9, SpCas9-HF1). In other embodiments, the RNA-guided endonuclease can be Cpf1.

The term "CRISPR" (Clustered Regularly Interspaced Short Palindromic Repeats) refers to certain genetic loci encoding factors of class I, II, or III DNA cleavage systems, for example, used by bacterial and archaeal cells to destroy foreign DNA (Horvath and Barrangou, Science 327:167-170). Components of CRISPR systems are taken advantage of herein in a heterologous manner for DNA targeting in cells.

The terms "type II CRISPR system" and "type II CRISPR-Cas system" are used interchangeably herein and refer to a DNA cleavage system utilizing a Cas9 endonuclease in complex with at least one RNA component. For example, a Cas9 can be in complex with a CRISPR RNA (crRNA) and a trans-activating CRISPR RNA (tracrRNA). In another example, a Cas9 can be in complex with a guide RNA. Thus, crRNA, tracrRNA, and guide RNA are non-limiting examples of RNA components herein.

The term CRISPR-associated ("Cas") endonuclease herein refers to a Cas protein encoded by a Cas gene. A Cas endonuclease, when in complex with a suitable RNA component, is capable of cleaving all or part of a specific DNA target sequence in certain embodiments. For example, it can be capable of introducing a single- or double-stranded break in a specific DNA target sequence; it can alternatively be characterized as being able to cleave one or both strands of a specific DNA target sequence. A Cas endonuclease can unwind the DNA duplex at the target sequence and cleaves at least one DNA strand, as mediated by recognition of the target sequence by a crRNA or guide RNA that is in complex with the Cas. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. A preferred Cas protein of the invention is Cas9.

As used herein, the term "protospacer adjacent motif (PAM)" refers to a short DNA sequence that is required for compatibility with the specific RNA-guided endonuclease being used.

As used herein, the term "sequence specific targeting nucleic acid" refers to a nucleic acid molecule that has sequence complementarity to a specific sequence in the genome, which will guide the RNA-guided endonuclease to cut, inactive, delete, activate transcription of, or repress transcription of the genomic target. In some embodiments the sequence specific targeting nucleic acid can be a guide RNA.

As used herein, the term "guide RNA (gRNA)" refers to a ribonucleic acid molecule that has sequence complementarity to a specific sequence in the genome immediately or 1 base pair upstream of the PAM sequence. In some embodiments the gRNA can be 17, 18, 19, 20, 21, 22, 23, 24, 25, 26, 27 bases long.

As used herein, the term "gene editing" refers to changing the sequence of the genomic DNA of a specific gene by using the CRISPR-Cas9 system. In some embodiments, the gene editing can be gene deletion. In other embodiments the gene editing can be the addition of another DNA sequence so as to produce a fusion protein.

As used herein, the term "gene deletion" refers to deletion of an amount of the genomic DNA of that gene so as to render the gene inactivated and undetectable at the protein and/or the mRNA level. In some embodiments, the gene deletion can be carried out with the CRISPR-Cas9 system.

As used herein, the term "amphipathic peptide" refers to a peptide possessing both hydrophilic and hydrophobic properties. In preferred embodiments, the amphipathic peptide is an Endo-Porter peptide.

As used herein, the term "CriPs" refers to CRISPR-based complexes comprising a nucleic acid-guided endonuclease (e.g., a Cas9), a targeting or guide nucleic acid sequence (e.g., a guide RNA ("gRNA")) and an amphipathic helical peptide (e.g., Endo-Porter). In certain embodiments, the CriPs further comprise a cell-targeting aptamer. In certain embodiments, the gRNA, peptide and/or aptamer components may be conjugated to each other. In other embodiments, the gRNA, peptide and/or aptamer components may be non-covalently associated to each other. For example, the aptamer component may be conjugated to the N- or C-terminus of the peptide, e.g., either directly or via an intervening linker moiety. Exemplary linker moieties include non-cleavable thioether moieties and cleavable linker moieties. In certain embodiments, the aptamer-peptide is conjugated to the gRNA. In other embodiments, CriPs optionally include a glucan particle. For example, the gRNA, peptide and/or aptamer components may be encapsulated in a glucan particle to facilitate delivery to a subject. The term "CriP" is used interchangeably with the term "nucleic acid-guided endonuclease-sequence-specific targeting nucleic acid—Endo-Porter peptide complex."

As used herein, the term "transcriptional activator" refers to a peptide, protein, or protein domain that can increase the transcription of certain target genes. In some embodiments the transcriptional activator can be associated with a nucleic acid-guided endonuclease.

As used herein, the term "transcriptional repressor" refers to a peptide, protein, or protein domain that can decrease the transcription of certain target genes.

As used herein, the term "type 2 diabetes" refers to a metabolic disease that is characterized by high blood sugar, insulin resistance or glucose intolerance, and a relative lack of insulin. In some embodiments, type 2 diabetes can include one or more of the co-morbidities from the group comprising: cardiovascular disease, retinopathy, kidney failure, neuropathy, periodontal disease, and non-alcoholic fatty liver disease.

As used herein, the term "prediabetes" refers to the precursor stage prior to the onset of diabetes mellitus in which not all of the symptoms required to diagnose diabetes are present, but blood sugar is abnormally high. Impaired fasting glycemia and impaired glucose tolerance are two forms of prediabetes that are similar in clinical definition (glucose levels that too high for their context) but are physiologically distinct (Disse, E; et al. (2013), "Heterogeneity of pregnancy outcomes and risk of LGA neonates in Caucasian females according to IADPSG criteria for gestational diabetes mellitus," Diabetes Metab, 39 (2): 132-138, doi:10.1016/j.diabet.2012.09.006). Insulin resistance, the insulin resistance syndrome (metabolic syndrome or syndrome X), and prediabetes are closely related to one another and have overlapping aspects.

As used herein, the terms "gestational diabetes" and "gestational diabetes mellitus (GDM)" are defined as any degree of glucose intolerance with onset or first recognition during pregnancy (Metzger B E, Coustan D R (Eds.): Proceedings of the Fourth International Work-shop-Conference on Gestational Diabetes Mellitus. Diabetes Care 21 (Suppl. 2): B1-B167, 1998). The definition applies whether insulin or only diet modification is used for treatment and whether or not the condition persists after pregnancy. It does not exclude the possibility that unrecognized glucose intolerance may have antedated or begun concomitantly with the pregnancy. Approximately 7% of all pregnancies are complicated by gestational diabetes, resulting in more than 200,000 cases annually. The prevalence may range from 1 to 14% of all pregnancies, depending on the population studied and the diagnostic tests employed.

As used herein, the term "glucose tolerance" refers to the process of metabolizing glucose in a subject. A low glucose tolerance is a key indicator and key symptom of type 2 diabetes. Glucose tolerance is routinely measured by the fasting glucose test which is common practice to those in the art.

As used herein, the term "UPC1 repressor" refers to any factor or protein in the genome that is known to or found to repress the expression or activity of UPC1. In some embodiments, a UPC1 repressor can be RIP140.

As used herein, the term "fused" refers to at least 2 proteins, protein domains, or peptides fused together to create a fusion protein. The fusion protein is created by recombinant DNA methods and expressed in and purified from a host bacterium. In some embodiments, the RNA-guided endonuclease can be fused to a transcriptional activator, including VP64. In other embodiments the RNA-guided recombinant endonuclease can be fused to a transcriptional repressor, including KRAB.

As used herein, the term "therapeutically effective amount" refers to an amount of the composition that is effective in achieving the desired outcome and non-toxic to the subject. In some embodiments, the therapeutically effective amount can be defined by the level of glucose tolerance in a subject.

Amphipathic Peptides

In a preferred aspect of the invention, amphipathic peptides are utilized in the CriPs described herein. The term "amphipathic" means that the peptide contains both polar (water-soluble or "water-loving") and nonpolar (non-water-soluble) portions or amino acids in its sequence. Preferred peptides comprise or consist of a combination of non-polar and polar amino acids arranged in pattern, e.g., an alternating pattern, such that the amino acids form a helical structure in which polar residues make up a weakly basic "face" of the peptide and non-polar (or hydrophobic) residues make up a lipophilic "face" of the structure Amino acids of the weakly basic "face" can include histidines (H) or lysine (K) Amino acids of the lipophilic "face" can include leucine (L). Such peptides can facilitate endocytosis-mediated delivery of cargoes or payloads, in particular, nucleic acid payloads, e.g., gRNAs.

As used herein, the term "endocytosis" refers to the cellular process of invagination and pinching off of the plasma membrane of a cell to form an enclosed vesicle (an endosome) within the cytosolic compartment of the cell, with said endosome being subsequently acidified by proton pumps embedded in the endosomal membrane. This invagination process results in engulfment of substances bound to the outer face of the plasma membrane and/or substances present in the extracellular medium. The term "endocytosis" as used herein can also include related processes, such as pinocytosis and potocytosis, that accomplish a similar engulfment followed by acidification.

The amphipathic peptides of the invention can form a two-face structure (i.e., 3-dimensional structure), with one face composed predominantly (80% to 100%) of aliphatic lipophilic amino acids (e.g. leucines), and another face composed predominantly (80% to 100%) of basic amino acids (e.g., histidines), preferably, with at least 70% of the amino acids of the weak-base face being histidines. At neutral pH, such as within the cytosol of cells, the amphipathic peptides can exist in a state which binds but does not permeabilize membranes, while at acidic pH, such as within endosomes, the amphipathic peptides can reversibly convert to a polycationic state effective to permeabilize cell membranes.

The amphipathic peptides of the invention typically have a length of about 5 to about 30 residues, e.g., about 5 to about 10 residues, about 5 to about 15 residues, about 5 to about 20 residues, about 5 to about 25 residues, about 10 to about 15 residues, about 10 to about 20 residues, about 10 to about 25 residues, about 15 to about 20 residues or about 15 to about 25 residues. In particular exemplary embodiments, the amphipathic peptides of the invention typically have a length of about 5 to about 20 residues, e.g., about 5 to about 10 residues, about 5 to about 15 residues, about 5 to about 20 residues, about 10 to about 15 residues, about 10 to about 20 residues, or about 15 to about 20 residues, for example, 10, 11, 12, 13, 14, 15, 16, 17, 18, 19 or 20 residues. The "about" when referencing peptide length means plus or minus 1 or 2 residues to or from the referenced integer or number of residues. Of exemplary interest are peptides which are modified, e.g., shortened, versions of the amphipathic peptides described in U.S. Pat. No. 7,084,248. For example, shortened versions of peptides having the sequences LHHLLHHLLHHLHHLLHHLHHLLHHL (SEQ ID NO: 5), LHKLLHHLLHKLHHLLHKLHH-LLHHL (SEQ ID NO: 7), or LHKLLHHLLHHLHKL-LHHLHHLLHKL (SEQ ID NO: 6) can be used in the methods and compositions of the instant invention. Details regarding said peptides can be found, for example, in U.S. Pat. No. 7,084,248.

Amphipathic peptides of the invention can comprise or consist of variations of lipophilic or hydrophobic residues (e.g., leucine (L)) and basic or weakly basic residues (e.g., histidine (H) or lysine (K)). In exemplary embodiments, the amphipathic peptides have about 50% lipophilic or hydrophobic residues (e.g., leucine (L)) and 50% basic or weakly basic residues (e.g., histidine (H) or lysine (K)). In some embodiments, the amphipathic peptides have about 40% lipophilic or hydrophobic residues (e.g., leucine (L)) and 60% basic or weakly basic residues (e.g., histidine (H) or lysine (K)). In other embodiments, the amphipathic peptides have about 60% lipophilic or hydrophobic residues (e.g., leucine (L)) and 40% basic or weakly basic residues (e.g., histidine (H) or lysine (K)).

In certain embodiments, amphipathic peptides of the invention comprise lipophilic or hydrophobic residues that are patterned in pairs, with several alternating pairs of lipophilic or hydrophobic residues, optionally with single lipophilic or hydrophobic residues occurring between some pairs of like residues within the peptides. This pattern allows the amphipathic peptides to form a helical structure in which polar residues make up a weakly basic "face" of the peptide and non-polar (or hydrophobic) residues make up a lipophilic "face" of the structure. Amino acids of the weakly basic "face" can include histidine (H) or lysine (K). Preferably, about 65-95% (e.g., about 70-95%, about 75-95%, about 75-95%, about 80-95%, about 85-95% or about 90-95%) of the residues of said amphipathic peptides are within pairs, adjacent pairs or pairs separated by, for example, a single residue of an alternate class type. In the above exemplary embodiments, as lysine is more basic, such residues should preferably constitute no greater than 10-25%, e.g., no greater than 15%, 20% or 25% of the total number of residues of the peptide (the remaining basic residues being, for example, H). An exemplary formula for the above amphipathic peptides is Exemplary peptides are as follows:

```
H2N-LHHLLHHLLHHLHHLLHHLHHLLHHL-COOH,

H2N-LHKLLHHLLHHLHKLLHHLHHLLHKL-COOH,

H2N-LHKLLHHLLHKLHHLLHKLHHLLHHL-COOH,

H2N-LHHLLHHLLHHLHHL-COOH,

H2N-HHLLHHLHHLLHHL-COOH,

H2N-LHLLHHLLHHLHHL-COOH,

H2N-LHHLLHLLHHLLHHL-COOH,

H2N-LHKLLHHLLHHLHK-COOH,

H2N-LHKLLHHLHHLLHKL-COOH,

H2N-KLHHLLHKLHHLLHH-COOH,

H2N-HLHLLHHLLHH-COOH,

H2N-LHLLHHLLHH-COOH,

H2N-LHKLLHHLLHKLHHL-COOH,

H2N-LHLLHH-COOH,

H2N-LHHLL-COOH,
and

H2N-LHKLL-COOH.
```

In a preferred embodiment, an amphipathic peptide is an Endo-Porter (EP) peptide. As used herein, an "Endo-Porter" or "EP" peptide is an amphipathic α-helical peptide with one face composed predominantly of aliphatic lipophilic amino acids, and the other face composed of basic amino acids. (Summerton J. E. (2005) Endo-Porter: a novel reagent for safe, effective delivery of substances into cells. Ann. N Y Acad. Sci. 1058:62-75, incorporated herein by reference). Endo-Porter is commercially available from Gene Tools, LLC (Philomath, Oreg.), and is incorporated herein by reference.

Exemplary amphipathic peptides have standard amino terminal and/or carboxy-terminal ends, but are readily amenable to any of the conjugation chemistries described below (or other art-recognized conjugation chemistries). Exemplary peptide conjugation is achieved through N-terminal and/or side chain amino groups, e.g., those found in lysine.

In certain embodiments, amphipathic peptides are functionalized at the C-terminus, for example, to include a C-terminal amide, —COHN$_2$. Without being bound in theory, the amide-functionalized C-terminus converts it from an anionic carboxyl to a non-ionic amide. This can potentially affect the delivery efficiency of the complexes described herein.

An amphipathic peptide can be modified, if desired, to render it even more capable of carrying a nucleic acid-guided endonuclease and/or a sequence-specific targeting nucleic acid from outside a cell to inside a cell. For example, an amphipathic peptide can be modified to have a lipid group at either its N- or C-terminus. Suitable lipid groups herein include acyl groups such as stearyl and myristyl groups. Other examples of lipid groups are acyl groups with 8, 9, 10, 11, 12, 13, 14, 15, 16, 17, or 18 carbons. Conditions for modifying peptides with lipid groups useful herein are disclosed in Regberg et al. (Int. J. Pharm.464:111-116) and Anko et al. (Biochim. Biophys. Acta Biomembranes 1818: 915-924) for example, which are incorporated herein by reference.

In certain embodiments, a nucleic acid-guided endonuclease component and at least one amphipathic peptide can be covalently linked to each other in a nucleic acid-guided endonuclease protein-amphipathic peptide complex. For example, a nucleic acid-guided endonuclease component and at least one amphipathic peptide can be fused together in a single amino acid sequence (i.e., a nucleic acid-guided endonuclease component and at least one amphipathic peptide can be comprised within a fusion protein). Thus, an example of covalent linkage herein can be via a peptide bond in which the amino acid sequence of a nucleic acid-guided endonuclease component is fused with the amino acid sequence of an amphipathic peptide, such that both these amino acid sequences are contained in a single amino acid sequence. Such a fusion protein can be characterized as a nucleic acid-guided endonuclease-amphipathic peptide fusion. In those embodiments in which an RNA component is associated with a nucleic acid-guided endonuclease component, such a fusion protein can be characterized as a nucleic acid-guided endonuclease-sequence-specific targeting nucleic acid-amphipathic peptide fusion. One or more amphipathic peptides can be located at the N-terminus or C-terminus of a nucleic acid-guided endonuclease-amphipathic peptide fusion, for example. Alternatively, one or more amphipathic peptides can be located at both the N- and C-termini of a nucleic acid-guided endonuclease-amphipathic peptide fusion. In another alternative, one or more amphipathic peptides can be located within the amino acid sequence of a nucleic acid-guided endonuclease-amphipathic peptide fusion. Embodiments herein comprising more than one amphipathic peptide can comprise at least 2, 3, 4, 5, 6, 7, 8, 9, 10, 11, 12, 13, 14, 15, 16, 17, 18, 19, or 20 amphipathic peptides, or 5-10, 5-20, or 10-20 amphipathic peptides. The amphipathic peptides fused to the nucleic acid-guided endonuclease component can be the same or different (e.g., 2, 3, 4, or more different types of amphipathic peptides). One or more amphipathic peptides can be fused directly to the amino acid sequence of a nucleic acid-guided endonuclease, and/or can be fused to a heterologous domain(s) (e.g., NLS or other organelle-targeting sequence such as an MTS) that is fused with a nucleic acid-guided endonuclease protein.

A fusion between an amphipathic peptide and a nucleic acid-guided endonuclease component can be direct (i.e., an amphipathic peptide amino acid sequence is directly linked to a nucleic acid-guided endonuclease amino acid sequence by a peptide bond). Alternatively, a fusion between an amphipathic peptide and a nucleic acid-guided endonuclease component can be via an intermediary amino acid sequence (this is an example of an amphipathic peptide and nucleic acid-guided endonuclease component being indirectly linked). Examples of an intermediary amino acid sequence include suitable linker sequences comprising at least 1, 2, 3, 4, 5, 6, 7, 8, 9, 10, 11, 12, 13, 14, 15, 16, 17, 18, 19, 20, 30, 40, 50, 60, 70, 80, 90, or 100 amino acid residues such as glycine, serine, alanine and/or proline. Suitable amino acid linkers are disclosed in U.S. Pat. Nos. 8,828,690, 8,580,922 and 5,990,275, for example, which are incorporated herein by reference. Other examples of intermediary amino acid sequences can comprise one or more other types of proteins and/or domains. For example, a marker protein (e.g., a fluorescent protein such as any of those disclosed herein) can be comprised in an intermediary amino acid sequence.

Nucleic Acid-Guided Endonucleases

Any guided endonuclease can be used in the methods and compositions disclosed herein. Such endonucleases include, but are not limited to Cas9 and Cpf1 endonucleases. Many endonucleases have been described to date that can recognize specific PAM sequences (see for example Zetsche B et al. 2015. Cell 163, 1013) and cleave the target DNA at a specific positions. It is understood that based on the methods and embodiments described herein utilizing a guided Cas system, one can now tailor these methods such that they can utilize any guided endonuclease system.

"Cas9" (formerly referred to as Cas5, Csn1, or Csx12) herein refers to a Cas endonuclease of a type II CRISPR system that forms a complex with crRNA and tracrRNA, or with a guide RNA, for specifically recognizing and cleaving all or part of a DNA target sequence. Cas9 protein comprises an RuvC nuclease domain and an HNH (H-N-H) nuclease domain, each of which cleaves a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, Cell 157:1262-1278). "Apo-Cas9" refers to Cas9 that is not complexed with an RNA component. Apo-Cas9 can bind DNA, but does so in a non-specific manner, and cannot cleave DNA (Sternberg et al., Nature 507:62-67).

The term "targeting nucleic acid" refers to, e.g., an RNA component of a CriP that is complementary to a strand of a DNA target sequence. This complementary sequence is referred to herein as a "guide sequence" or a "sequence-specific targeting nucleic acid" sequence. Examples of suitable targeting nucleic acids include crRNA and guide RNA. RNA components in certain embodiments (e.g., guide RNA alone, crRNA+tracrRNA) can render CriP competent for specific DNA targeting.

The term "CRISPR RNA" (crRNA) refers to an RNA sequence that can form a complex with one or more Cas proteins (e.g., Cas9) and provides DNA binding specificity to the complex. A crRNA provides DNA binding specificity since it contains "guide sequence" ("variable targeting domain" [VT]) that is complementary to a strand of a DNA target sequence. A crRNA further comprises a "repeat sequence" ("tracr RNA mate sequence") encoded by a repeat region of the CRISPR locus from which the crRNA was derived. A repeat sequence of a crRNA can anneal to sequence at the 5'-end of a tracrRNA. crRNA in native CRISPR systems is derived from a "pre-crRNA" transcribed from a CRISPR locus. A pre-crRNA comprises spacer regions and repeat regions; spacer regions contain unique sequence complementary to a DNA target site sequence. Pre-crRNA in native systems is processed to multiple different crRNAs, each with a guide sequence along with a portion of repeat sequence. CRISPR systems utilize crRNA, for example, for DNA targeting specificity.

The term "trans-activating CRISPR RNA" (tracrRNA) refers to a non-coding RNA used in type II CRISPR systems which contains, in the 5'-to-3' direction, (i) a sequence that anneals with the repeat region of CRISPR type II crRNA and (ii) a stem loop-containing portion (Deltcheva et at, Nature 471:602-607).

The terms "guide RNA" (gRNA) and "single guide RNA" (sgRNA) are used interchangeably herein. A gRNA herein can refer to a chimeric sequence containing a crRNA operably linked to a tracrRNA. Alternatively, a gRNA can refer to a synthetic fusion of a crRNA and a tracrRNA, for example. A gRNA can also be characterized in terms of having a guide sequence (variable targeting domain) followed by a Cas endonuclease recognition (CER) domain A CER domain can comprise a tracrRNA mate sequence followed by a tracrRNA sequence.

A "CRISPR DNA" (crDNA) can optionally be used instead of an RNA component. A crDNA has a DNA sequence corresponding to the sequence of a crRNA as disclosed herein. A crDNA can be used with a tracrRNA in a crDNA/tracrRNA complex, which in turn can be associated with a nucleic acid-guided endonuclease component. It is contemplated that any disclosure herein regarding a crRNA can similarly apply to using a crDNA, accordingly. Thus, in embodiments herein incorporating a crDNA, a nucleic acid-guided endonuclease could instead be referred to as a complex comprising at least one Cas protein and at least one crDNA.

Certain embodiments of the disclosed invention can be used to deliver a nucleic acid-guided endonuclease already associated (pre-associated) with an RNA component into a cell. Such embodiments may avoid the need to deliver a DNA construct into cells for expressing a nucleic acid-guided endonuclease RNA component, thus averting any potentially unwanted effects of introducing exogenous DNA into cells. The disclosed invention is flexible, however, since in certain other embodiments an RNA component can be provided (e.g., expressed) in a cell into which a nucleic acid-guided endonuclease RNA component protein-amphipathic peptide complex is being delivered. An RNA component provided in this manner can associate with a nucleic acid-guided endonuclease RNA component after delivery/entry of the a nucleic acid-guided endonuclease RNA component-amphipathic peptide complex into the cell. Regardless of the mode of RNA component delivery, a nucleic acid-guided endonuclease RNA component-amphipathic peptide complex herein is able to associate with an RNA component, forming a nucleic acid-guided endonuclease RNA component-amphipathic peptide complex that can target a specific DNA sequence in the cell. Thus, the disclosed invention offers substantial flexibility for providing a nucleic acid-guided endonuclease in cells to perform nucleic acid-guided endonuclease-mediated DNA targeting.

Compositions disclosed in certain embodiments comprise at least one protein component of a nucleic acid-guided endonuclease RNA component. A nucleic acid-guided endonuclease RNA component can refer to a Cas protein such as Cas9. Examples of suitable Cas proteins include one or more Cas endonucleases of type I, II, or III CRISPR systems (Bhaya et al., Annu. Rev. Genet.45:273-297, incorporated herein by reference). A type I CRISPR Cas protein can be a Cas3 or Cas4 protein, for example. A type II CRISPR Cas protein can be a Cas9 protein, for example. A type III CRISPR Cas protein can be a Cas10 protein, for example. A Cas9 protein is used in certain preferred embodiments. A Cas protein in certain embodiments may be a bacterial or archaeal protein. Type I-III CRISPR Cas proteins herein are typically prokaryotic in origin; type I and III Cas proteins can be derived from bacterial or archaeal species, whereas type II Cas proteins (i.e., a Cas9) can be derived from bacterial species, for example. In other embodiments, suitable Cas proteins include one or more of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

In other aspects of the disclosed invention, a Cas protein herein can be from any of the following genera: *Aeropyrum, Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella,* or *Thermotoga*. Alternatively, a Cas protein herein can be encoded, for example, by any of SEQ ID NOs:462-465, 467-472, 474-477, 479-487, 489-492, 494-497, 499-503, 505-508, 510-516, or 517-521 as disclosed in U.S. Appl. Publ. No. 2010/0093617, which is incorporated herein by reference.

A nucleic acid-guided endonuclease RNA component can comprise a Cas9 amino acid sequence, for example. A nucleic acid-guided endonuclease RNA component comprising this type of protein component typically can be characterized as having Cas9 as the endonuclease component of the nucleic acid-guided endonuclease RNA component. The amino acid sequence of a Cas9 protein herein, as well as certain other Cas proteins herein, may be derived from *Streptococcus* (e.g., *S. pyogenes, S. pneumoniae, S. thermophilus, S. agalactiae, S. parasanguinis, S. oralis, S. salivarius, S. macacae, S. dysgalactiae, S. anginosus, S. constellatus, S. pseudoporcinus, S. mutans*), *Listeria* (e.g., *L. innocua*), *Spiroplasma* (e.g., *S. apis, S. syrphidicola*) Peptostreptococcaceae, *Atopobium, Porphyromonas* (e.g., *P. catoniae*), *Prevotella* (e.g., *P. intermedia*), *Veillonella, Treponema* (e.g., *T. socranskii, T. denticola*), *Capnocytophaga, Finegoldia* (e.g., *F. magna*), Coriobacteriaceae (e.g., *C. bacterium*), *Olsenella* (e.g., *O. profusa*), *Haemophilus* (e.g., *H. sputorum, H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus, Bacillus* (e.g., *B. cereus*), *Aquimarina* (e.g., *A. muelleri*), *Chryseobacterium* (e.g., *C. palustre*), *Bacteroides* (e.g., *B.*

*graminisolvens*), *Neisseria* (e.g., *N. meningitidis*), *Francisella* (e.g., *F. novicida*), or *Flavobacterium* (e.g., *F. frigidarium, F. soli*) species, for example. An *S. pyogenes* Cas9 is preferred in certain aspects herein. As another example, a Cas9 protein can be any of the Cas9 proteins disclosed in Chylinski et al. (RNA Biology 10:726-737), which is incorporated herein by reference.

Accordingly, the sequence of a Cas9 protein herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03JI6 (*S. thermophilus*), EGP66723, EGS38969, EGV05092, EHI65578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJO19166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. A variant of any of these Cas9 protein sequences may be used, but should have specific binding activity, and optionally cleavage or nicking activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9.

Alternatively, a Cas9 protein herein can be encoded by any of SEQ ID NOs:462 (*S. thermophilus*), 474 (*S. thermophilus*), 489 (*S. agalactiae*), 494 (*S. agalactiae*), 499 (*S. mutans*), 505 (*S. pyogenes*), or 518 (*S. pyogenes*) as disclosed in U.S. Appl. Publ. No. 2010/0093617 (incorporated herein by reference), for example. Alternatively still, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing amino acid sequences, for example. Such a variant Cas9 protein should have specific binding activity, and optionally cleavage or nicking activity, toward DNA when associated with an RNA component herein.

The origin of a Cas protein used herein (e.g., Cas9) may be from the same species from which the RNA component(s) is derived, or it can be from a different species. For example, an nucleic acid-guided endonuclease comprising a Cas9 protein derived from a *Streptococcus* species (e.g., *S. pyogenes* or *S. thermophilus*) may be complexed with at least one RNA component having a sequence (e.g., crRNA repeat sequence, tracrRNA sequence) derived from the same *Streptococcus* species. Alternatively, the origin of a Cas protein used herein (e.g., Cas9) may be from a different species from which the RNA component(s) is derived (the Cas protein and RNA component(s) may be heterologous to each other). Such a heterologous Cas/RNA component should have DNA targeting activity.

Determining binding activity and/or endonucleolytic activity of a Cas protein herein toward a specific target DNA sequence may be assessed by any suitable assay known in the art, such as disclosed in U.S. Pat. No. 8,697,359, which is disclosed herein by reference. A determination can be made, for example, by expressing a Cas protein and suitable RNA component in a cell, and then examining the predicted DNA target site for the presence of an indel (a Cas protein in this particular assay would typically have complete endonucleolytic activity (double-strand cleaving activity)). Examining for the presence of an alteration/modification (e.g., indel) at the predicted target site could be done via a DNA sequencing method or by inferring alteration/modification formation by assaying for loss of function of the target sequence, for example. In another example, Cas protein activity can be determined by expressing a Cas protein and suitable RNA component in a cell that has been provided a donor DNA comprising a sequence homologous to a sequence in at or near the target site. The presence of donor DNA sequence at the target site (such as would be predicted by successful HR between the donor and target sequences) would indicate that targeting occurred. In still another example, Cas protein activity can be determined using an in vitro assay in which a Cas protein and suitable RNA component are mixed together along with a DNA polynucleotide containing a suitable target sequence. This assay can be used to detect binding (e.g., gel-shift) by Cas proteins lacking cleavage activity, or cleavage by Cas proteins that are endonucleolytically competent.

A Cas protein such as a Cas9 can further comprise a heterologous nuclear localization sequence (NLS) in certain aspects. A heterologous NLS amino acid sequence may be of sufficient strength to drive accumulation of a Cas protein, or Cas protein-amphipathic peptide complex, in a detectable amount in the nucleus of a cell, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein, for example. Two or more NLS sequences can be linked to a Cas protein, for example, such as on both the N- and C-termini of a Cas protein. Non-limiting examples of suitable NLS sequences include those disclosed in U.S. Pat. Nos. 6,660,830 and 7,309,576 (e.g., Table 1 therein), which are both incorporated herein by reference. A Cas protein as disclosed herein can be fused with an amphipathic peptide, for example. It would be understood that such a Cas-amphipathic peptide fusion protein can also comprise an NLS as described above. It would also be understood that, in embodiments in which a Cas protein is fused with an amino acid sequence targeting a different organelle (e.g., mitochondria), such a Cas protein typically would not contain an NLS. In certain embodiments, a Cas protein and its respective RNA component (e.g., crRNA) that directs DNA-specific targeting by the Cas protein can be heterologous to a cell, in particular a non-prokaryotic cell. The heterologous nature of these nucleic acid-guided endonuclease RNA components is due to that Cas proteins and their respective RNA components are only known to exist in prokaryotes (bacteria and archaea).

In some embodiments, a Cas protein is part of a fusion protein comprising one or more heterologous protein domains (e.g., 1, 2, 3, or more domains in addition to the Cas protein). These embodiments can encompass a Cas protein that is covalently linked to an amphipathic peptide and one or more additional heterologous amino acid sequences, for example. Other embodiments can encompass a Cas protein that is covalently linked to one or more additional heterologous amino acid sequences not including an amphipathic peptide, for example (an amphipathic peptide would be non-covalently linked to a Cas fusion protein in such embodiments). A fusion protein comprising a Cas protein may comprise any additional protein sequence, and optionally a linker sequence between any two domains, such as between Cas and a first heterologous domain. Examples of protein domains that may be fused to a Cas protein include, without limitation, epitope tags (e.g., histidine (His, polyhistidine), V5, FLAG, influenza hemagglutinin (HA), myc, VSV-G, thioredoxin (Trx)), reporters (e.g., glutathione-5-transferase (GST), horseradish peroxidase (HRP), chloramphenicol acetyltransferase (CAT), beta-galactosidase, beta-glucuronidase (GUS), luciferase, green fluorescent protein (GFP), HcRed, DsRed, cyan fluorescent protein (CFP), yellow fluorescent protein (YFP), blue fluorescent protein (BFP)), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein in other embodiments may be in fusion with a protein that binds DNA molecules or other molecules, such as maltose binding protein (MBP), S-tag, Lex A DNA binding domain (DBD), GAL4A DNA binding domain, and herpes simplex virus (HSV) VP16. Additional domains that may be part of a fusion protein comprising a Cas protein are disclosed in U.S. Patent Appl. Publ. No. 2011/0059502, which is incorporated herein by reference. In certain embodiments in which a Cas protein is fused to a heterologous protein (e.g., a transcription factor), the Cas protein has DNA recognition and binding activity (when in complex with a suitable RNA component), but no DNA nicking or cleavage activity. A Cas protein as disclosed herein can be fused with an amphipathic peptide (an example of a Cas protein covalently linked to an amphipathic peptide), for example. It would be understood that such a Cas-amphipathic peptide fusion protein can also be fused with one or more heterologous domains as described above, if desired.

Other examples of heterologous domains that can be linked to a Cas protein include amino acid sequences targeting the protein to a particular organelle (i.e., localization signal). Examples of organelles that can be targeted include mitochondria and chloroplasts. Typically, such targeting domains are used instead of an NLS when targeting extra-nuclear DNA sites. A mitochondrial targeting sequence (MTS) can be situated at or near the N-terminus of a Cas protein, for example. MTS examples are disclosed in U.S. Patent Appl. Publ. Nos. 2007/0011759 and 2014/0135275, which are incorporated herein by reference. A chloroplast targeting sequence can be as disclosed in U.S. Patent Appl. Publ. No. 2010/0192262 or 2012/0042412, for example, which are incorporated herein by reference.

The protein component of a nucleic acid-guided endonuclease can be associated with at least one RNA component (thereby constituting a complete a nucleic acid-guided endonuclease) that comprises a sequence complementary to a target site sequence on a chromosome or episome in a cell, for example. The nucleic acid-guided endonuclease in such embodiments can bind to the target site sequence, and optionally cleave one or both DNA strands at the target site sequence. A nucleic acid-guided endonuclease can cleave one or both strands of a DNA target sequence, for example. A nucleic acid-guided endonuclease can cleave both strands of a DNA target sequence in another example. It would be understood that in all these embodiments, a nucleic acid-guided endonuclease protein component can be covalently or non-covalently linked to at least one amphipathic peptide in a nucleic acid-guided endonuclease-amphipathic peptide complex. The association of a nucleic acid-guided endonuclease-amphipathic peptide complex with an RNA component can be characterized as forming a nucleic acid-guided endonuclease-amphipathic peptide complex. Any disclosure herein regarding a nucleic acid-guided endonuclease can likewise apply to a nucleic acid-guided endonuclease component of a nucleic acid-guided endonuclease-amphipathic peptide complex, unless otherwise noted.

A nucleic acid-guided endonuclease that can cleave both strands of a DNA target sequence typically comprises a Cas protein that has all of its endonuclease domains in a functional state (e.g., wild type endonuclease domains or variants thereof retaining some or all activity in each endonuclease domain) Thus, a wild type Cas protein (e.g., a Cas9 protein disclosed herein), or a variant thereof retaining some or all activity in each endonuclease domain of the Cas protein, is a suitable example of a nucleic acid-guided endonuclease that can cleave both strands of a DNA target sequence. A Cas9 protein comprising functional RuvC and HNH nuclease domains is an example of a Cas protein that can cleave both strands of a DNA target sequence. A nucleic acid-guided endonuclease that can cleave both strands of a DNA target sequence typically cuts both strands at the same position such that blunt-ends (i.e., no nucleotide overhangs) are formed at the cut site.

A nucleic acid-guided endonuclease that can cleave one strand of a DNA target sequence can be characterized herein as having nickase activity (e.g., partial cleaving capability). A Cas nickase (e.g., Cas9 nickase) typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain.

Non-limiting examples of Cas9 nickases suitable for use herein are disclosed by Gasiunas et al. (Proc. Natl. Acad. Sci. U.S.A. 109:E2579-E2586), Jinek et al. (Science 337: 816-821), Sapranauskas et al. (Nucleic Acids Res. 39:9275-9282) and in U.S. Patent Appl. Publ. No. 2014/0189896, which are incorporated herein by reference. For example, a Cas9 nickase can comprise an *S. thermophilus* Cas9 having an Asp-31 substitution (e.g., Asp-31-Ala) (an example of a mutant RuvC domain), or a His-865 substitution (e.g., His-865-Ala), Asn-882 substitution (e.g., Asn-882-Ala), or Asn-891 substitution (e.g., Asn-891-Ala) (examples of mutant HNH domains) Also for example, a Cas9 nickase can comprise an *S. pyogenes* Cas9 having an Asp-10 substitution (e.g., Asp-10-Ala), Glu-762 substitution (e.g., Glu-762-Ala), or Asp-986 substitution (e.g., Asp-986-Ala) (examples of mutant RuvC domains), or a His-840 substitution (e.g., His-840-Ala), Asn-854 substitution (e.g., Asn-854-Ala), or Asn-863 substitution (e.g., Asn-863-Ala) (examples of mutant HNH domains). Regarding *S. pyogenes* Cas9, the three RuvC subdomains are generally located at amino acid residues 1-59, 718-769 and 909-1098, respectively, and the HNH domain is located at amino acid residues 775-908 (Nishimasu et al., Cell 156:935-949).

A Cas9 nickase can be used for various purposes in cells, if desired. For example, a Cas9 nickase can be used to stimulate HR at or near a DNA target site sequence with a suitable donor polynucleotide. Since nicked DNA is not a substrate for NHEJ processes, but is recognized by HR processes, nicking DNA at a specific target site should render the site more receptive to HR with a suitable donor polynucleotide.

As another example, a pair of Cas9 nickases can be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a DSB (i.e., a DSB with single-stranded overhangs), which is then recognized as a substrate for NHEJ (leading to indel formation) or HR (leading to recombination with a suitable donor polynucleotide, if provided). Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins can be used in a Cas9 nickase pair as described above. For example, a Cas9 nickase with a mutant RuvC domain, but functioning HNH domain (i.e., Cas9 HNH+/RuvC−), could be used (e.g., *S. pyogenes* Cas9 HNH+/RuvC−). Each Cas9 nickase (e.g., Cas9 HNH+/RuvC−) would be directed to specific DNA sites nearby each other (up to 100 base pairs apart) by using suitable RNA components with guide RNA sequences targeting each nickase to each specific DNA site.

A nucleic acid-guided endonuclease in certain embodiments can bind to a DNA target site sequence, but does not cleave any strand at the target site sequence. Such a nucleic acid-guided endonuclease may comprise a Cas protein in which all of its nuclease domains are mutant, dysfunctional. For example, a Cas9 protein that can bind to a DNA target site sequence, but does not cleave any strand at the target site sequence, may comprise both a mutant, dysfunctional RuvC domain and a mutant, dysfunctional HNH domain Non-limiting examples of such a Cas9 protein comprise any of the RuvC and HNH nuclease domain mutations disclosed above (e.g., an *S. pyogenes* Cas9 with an Asp-10 substitution such as Asp-10-Ala and a His-840 substitution such as His-840-Ala). A Cas protein that binds, but does not cleave, a target DNA sequence can be used to modulate gene expression, for example, in which case the Cas protein could be fused with a transcription factor (or portion thereof) (e.g., a repressor or activator, such as any of those disclosed herein). For example, a Cas9 comprising an *S. pyogenes* Cas9 with an Asp-10 substitution (e.g., Asp-10-Ala) and a His-840 substitution (e.g., His-840-Ala) can be fused to a VP16 or VP64 transcriptional activator domain. The guide sequence used in the RNA component of such a nucleic acid-guided endonuclease would be complementary to a DNA sequence in a gene promoter or other regulatory element (e.g., intron), for example.

A nucleic acid-guided endonuclease can bind to a target site sequence, and optionally cleave one or both strands of the target site sequence, in a chromosome, episome, or any other DNA molecule in the genome of a cell. This recognition and binding of a target sequence is specific, given that an RNA component of the nucleic acid-guided endonuclease comprises a sequence (guide sequence) that is complementary to a strand of the target sequence. A target site in certain embodiments can be unique (i.e., there is a single occurrence of the target site sequence in the subject genome).

The length of a target sequence can be at least 13, 14, 15, 16, 17, 18, 19, 20, 21, 22, 23, 24, 25, 26, 27, 28, 29, or 30 nucleotides; between 13-30 nucleotides; between 17-25 nucleotides; or between 17-20 nucleotides, for example. This length can include or exclude a PAM sequence. Also, a strand of a target sequence has sufficient complementarity with a guide sequence (of a crRNA or gRNA) to hybridize with the guide sequence and direct sequence-specific binding of a Cas protein or Cas protein complex to the target sequence (if a suitable PAM is adjacent to the target sequence, see below). The degree of complementarity between a guide sequence and a strand of its corresponding DNA target sequence is at least about 90%, 91%, 92%, 93%, 94%, 95%, 96%, 97%, 98%, 99%, or 100%, for example. A target site may be located in a sequence encoding a gene product (e.g., a protein or an RNA) or a non-coding sequence (e.g., a regulatory sequence or a "junk" sequence), for example.

A PAM (Protospacer-Adjacent Motif) sequence may be adjacent to the target site sequence. A PAM sequence is a short DNA sequence recognized by a nucleic acid-guided endonuclease. The associated PAM and first 11 nucleotides of a DNA target sequence are likely important to Cas9/gRNA targeting and cleavage (Jiang et al., Nat. Biotech. 31:233-239). The length of a PAM sequence can vary depending on the Cas protein or Cas protein complex used, but is typically 2, 3, 4, 5, 6, 7, or 8 nucleotides long, for example. A PAM sequence is immediately downstream from, or within 2, or 3 nucleotides downstream of, a target site sequence that is complementary to the strand in the target site that is in turn complementary to an RNA component guide sequence, for example. In embodiments in which a nucleic acid-guided endonuclease is an endonucleolytically active Cas9 protein complexed with an RNA component, Cas9 binds to the target sequence as directed by the RNA component and cleaves both strands immediately 5' of the third nucleotide position upstream of the PAM sequence. Consider the following example of a target site: PAM sequence:

5'-NNNNNNNNNNNNNNNNNNNNNNN<u>N</u>NNXGG-3'.

N can be A, C, T, or G, and X can be A, C, T, or G in this example sequence (X can also be referred to as $N_{PAM}$). The PAM sequence in this example is XGG (underlined). A suitable Cas9/RNA component complex would cleave this target immediately 5' of the double-underlined N. The string of N's represents target sequence that is at least about 90%, 91%, 92%, 93%, 94%, 95%, 96%, 97%, 98%, 99%, or 100% identical, for example, with a guide sequence in an RNA component (where any T's of the DNA target sequence would align with any U's of the RNA guide sequence). A guide sequence of an RNA component of a Cas9 complex, in recognizing and binding at this target sequence (which is representative of target sites), would anneal with the complement sequence of the string of N's; the percent complementarity between a guide sequence and the target site complement is at least about 90%, 91%, 92%, 93%, 94%, 95%, 96%, 97%, 98%, 99%, or 100%, for example.

A PAM is typically selected in view of the type of nucleic acid-guided endonuclease being employed. A PAM sequence may be one recognized by a nucleic acid-guided endonuclease comprising a Cas, such as Cas9, derived from any of the species disclosed herein from which a Cas can be derived, for example. In certain embodiments, the PAM sequence may be one recognized by a nucleic acid-guided endonuclease comprising a Cas9 derived from *S. pyogenes, S. thermophilus, S. agalactiae, N. meningitidis, T. denticola,* or *F. novicida*. For example, a suitable Cas9 derived from *S. pyogenes* could be used to target genomic sequences having a PAM sequence of NGG (N can be A, C, T, or G). As other examples, a suitable Cas9 could be derived from any of the following species when targeting DNA sequences having the following PAM sequences: *S. thermophilus* (NNAGAA), *S. agalactiae* (NGG, NNAGAAW (W is A or T), NGGNG), *N. meningitidis* (NNNNGATT), *T. denticola* (NAAAAC), or *F. novicida* (NG) (where N in all these particular PAM sequences is A, C, T, or G). Other examples of Cas9/PAMs of the invention include those disclosed in Shah et al. (RNA Biology 10:891-899) and Esvelt et al. (Nature Methods 10:1116-1121), which are incorporated herein by reference.

An RNA component can comprise a sequence complementary to a target site sequence in a chromosome or episome in a cell. A nucleic acid-guided endonuclease can specifically bind to a target site sequence, and optionally cleave one or both strands of the target site sequence, based on this sequence complementary. Thus, the complementary sequence of an RNA component in certain embodiments of the disclosed invention can also be referred to as a guide sequence or variable targeting domain Guide Polynucleotides The complexes of the invention include a guide polynucleotide. As used herein, the term "guide polynucleotide," relates to a polynucleotide sequence that can form a complex with a nucleic acid-guided endonuclease and enables the nucleic acid-guided endonuclease to recognize and optionally cleave a DNA target site. The guide polynucleotide can be a single molecule or a double molecule. The guide polynucleotide sequence can be a RNA sequence, a DNA sequence, or a combination thereof (an RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization.

A guide polynucleotide that solely comprises ribonucleic acids is also referred to as a "guide RNA." The guide polynucleotide can be a double-stranded (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a nucleic acid-guided endonuclease. The CER domain of the double molecule guide polynucleotide comprises two separate molecules that are hybridized along a region of complementarity. The two separate strands can be RNA, DNA, and/or RNA-DNA combination sequences. In some embodiments, the first molecule of the duplex guide polynucleotide comprising a VT domain linked to a CER domain ("crNucleotide") is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides).

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA combination sequence. The VT domain and/or the CER domain of a single guide polynucleotide can comprise an RNA sequence, a DNA sequence, or an RNA-DNA combination sequence. In some embodiments, the single guide polynucleotide comprises a crNucleotide (comprising a VT domain linked to a CER domain) linked to a tracrNucleotide (comprising a CER domain), wherein the linkage is a nucleotide sequence comprising an RNA sequence, a DNA sequence, or an RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides).

Thus, a guide polynucleotide and a type II Cas endonuclease in certain embodiments can form a complex with each other (referred to as a "guide polynucleotide/Cas endonuclease complex" or also referred to as "guide polynucleotide/Cas endonuclease system"), wherein the guide polynucleotide/Cas endonuclease complex can direct the Cas endonuclease to target a genomic target site in a cell, optionally enabling the Cas endonuclease to introduce a single- or double-strand break into the genomic target site. A guide polynucleotide/Cas endonuclease complex can be linked to at least one amphipathic peptide, wherein such complex is capable of binding to, and optionally creating a single- or double-strand break to a target site of a cell.

The term "variable targeting domain" or "VT domain" is used interchangeably herein and refers to a nucleotide sequence that is complementary to one strand (nucleotide sequence) of a double strand DNA target site. The percent complementarity between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, an RNA sequence, a modified DNA sequence, a modified RNA sequence (see, e.g., modifications described herein), or any combination thereof.

The term "Cas endonuclease recognition domain" or "CER domain" of a guide polynucleotide is used interchangeably herein and relates to a nucleotide sequence (such as a second nucleotide sequence domain of a guide polynucleotide), that interacts with a Cas endonuclease polypeptide. A CER domain can be composed of a DNA sequence, an RNA sequence, a modified DNA sequence, a modified RNA sequence (see, e.g., modifications described herein), or any combination thereof. The terms "target site," "target sequence," "target DNA," "DNA target sequence," "target locus," "protospacer" and the like are used interchangeably herein. A target site sequence refers to a polynucleotide sequence on a chromosome, episome, or any other DNA molecule in the genome of a cell to which a nucleic acid-guided endonuclease can recognize, bind to, and optionally nick or cleave. A target site can be (i) an endogenous/native site in the cell, (ii) heterologous to the cell and therefore not be naturally occurring in the genome, or (iii) found in a heterologous genomic location compared to where it natively occurs.

A target site sequence herein is at least 13 nucleotides in length and has a strand with sufficient complementarity to a guide sequence (of a crRNA or gRNA) to be capable of hybridizing with the guide sequence and direct sequence-specific binding of a nucleic acid-guided endonuclease or a nucleic acid-guided endonuclease complex to the target sequence (if a suitable PAM is adjacent to the target sequence in certain embodiments). A cleavage/nick site (applicable with a endonucleolytic or nicking Cas) can be within the target sequence (e.g., using a Cas9) or a cleavage/nick site could be outside of the target sequence (e.g., using a Cas9 fused to a heterologous endonuclease domain such as one derived from a FokI enzyme). It is also possible for a target site sequence to be bound by a nucleic acid-guided endonuclease lacking cleavage or nicking activity.

A guide sequence can comprise one or more modifications (e.g., a base modification, a backbone modification), to provide the nucleic acid with a new or enhanced feature (e.g., improved stability). A guide sequence can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming guide sequences, the phosphate groups can covalently link adjacent nucleosides to one another to form a linear polymeric compound. In addition, linear compounds may have internal nucleotide base complementarity and may therefore fold in a manner as to produce a fully or partially double-stranded compound. Within guide sequences, the phosphate groups can commonly be referred to as forming the internucleoside backbone of the guide sequence. The linkage or backbone of the guide sequence can be a 3' to 5' phosphodiester linkage.

A guide sequence can comprise nucleoside analogs, which are oxy- or deoxy-analogues of the naturally-occurring DNA and RNA nucleosides deoxycytidine, deoxyuridine, deoxyadenosine, deoxyguanosine and thymidine. A guide sequence can also include a universal base, such as deoxyinosine, or 5-nitroindole.

A guide sequence can comprise a modified backbone and/or modified internucleoside linkages. Modified backbones can include those that retain a phosphorus atom in the backbone and those that do not have a phosphorus atom in the backbone.

Suitable modified guide sequence backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoallcylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable guide sequences having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

A guide sequence can comprise one or more phosphorothioate and/or heteroatom internucleoside linkages, in particular —CH2-NH—O—CH$_2$—, —CH$_2$—N(CH$_3$)—O—CH$_2$— (i.e. a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—).

A guide sequence can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A guide sequence can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

A guide sequence can comprise a nucleic acid mimetic. The term "mimetic" includes polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A guide sequence can comprise linked morpholino units (i.e. morpholino nucleic acid) having heterocyclic bases attached to the morpholino ring Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of guide sequences. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA 4,4'-dimethoxytrityl (DMT) protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bridged bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties. Another useful modification includes unlocked nucleic acid (UNA) monomers, which are acyclic derivatives of RNA lacking the C2'-C3'-bond of the ribose ring of RNA. The missing bond increases the flexibility of the molecule, decreasing duplex thermo stability.

A guide sequence can comprise one or more substituted sugar moieties. Suitable polynucleotides can comprise a sugar substituent group selected from: OH; F; —O, S—, or N-alkyl; O—, S—, or N-alkenyl; O—, S— or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly suitable are $O((CH_2)_nO)$ $mCH_3$, $O(CH_2)_nOCH_3$, $O(CH_2)_nNH_2$, $O(CH_2)_nCH_3$, $O(CH_2)—ONH_2$, and $O(CH_2)_nON((CH_2)_nCH_3)_2$, where n and m are from 1 to about 10. A sugar substituent group can be selected from: C1 to C10 lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an guide sequence, or a group for improving the pharmacodynamic properties of a guide sequence, and other substituents having similar properties. A suitable modification can include 2'-methoxyethoxy (2'-O—$CH_2CH_2OCH_3$, also known as 2'-O-(2-methoxyethyl) or 2'-MOE i.e., an alkoxyalkoxy group). A further suitable modification can include 2'-dimethylaminooxyethoxy, (i.e., a $O(CH_2)_2O$ $N(CH_3)_2$ group, also known as 2'-DMAOE), and 2'-dimethylaminoethoxyethoxy (also known as 2'-O-dimethyl-aminoethoxy-ethyl or 2'-DMAEOE), i.e., 2'-O—$(CH_2)_2$—O—$(CH_2)_2$—$N(CH_3)_2$.

Other suitable sugar substituent groups can include methoxy (—O—$CH_3$), aminopropoxy (—O $CH_2$ $CH_2$ $CH_2NH_2$), allyl (—$CH_2$—CH=$CH_2$), —O-allyl (—O— $CH_2$—CH=$CH_2$) and fluoro (F). 2'-sugar substituent groups may be in the arabino (up) position or ribo (down) position. A suitable 3'-arabino modification is 2'-F. Similar modifications may also be made at other positions on the oligomeric compound, particularly the 3' position of the sugar on the 3' terminal nucleoside or in 2'-5' linked nucleotides and the 5' position of 5' terminal nucleotide. Oligomeric compounds may also have sugar mimetics such as cyclobutyl moieties in place of the pentofuranosyl sugar.

A guide sequence may also include nucleobase (often referred to simply as "base") modifications or substitutions. "Unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminopurine, 2,6-diaminopurine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil found in pseudouridine), 5-hydroxybutynl-2'-deoxyuridine, 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2 (3H)-one), G-clamps such as a substituted phenoxazine cytidine (e.g. 9-(2-aminoethoxy)-H-pyrimido(5,4-(b) (1,4) benzoxazin-2(3H)-one), carbazole cytidine (2H-pyrimido(4, 5-b)indol-2-one), pyridoindole cytidine (Hpyrido(3',2':4,5) pyrrolo(2,3-d)pyrimidin-2-one).

Heterocyclic base moieties can include those in which the purine or pyrimidine base is replaced with other heterocycles, for example 7-deaza-adenine, 7-deazaguanosine, 8-aza-7-deazaguanosine, 2-aminopyridine, and 2-pyridone; isoG and isoC and hydrophobic non-natural bases such thioisoquinolines/isocarbostyrils (SICS) (Seo et al. Journal of American Chemical Society 2009 p 3246-52). Nucleobases can be useful for increasing the binding affinity of a polynucleotide compound. These can include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

In some embodiments, the guide sequences comprise one or more sugar modifications (2'), such as a 2'-O—$CH_3$, a 2'-F, a 2'-MOE modification. In some embodiments, guide sequences can comprise one or more modified bases, such as a LNA, a UNA, deoxyuridine, pseudouridine, 5-methylcytosine, 2-aminopurine, 2,6-diaminopurine, deoxyinosine, 5-hydroxybutynl-2'-deoxyuridine, 8-aza-7-deazaguanosine, or 5-nitroindole. In some embodiments, guide sequences comprise one or more sugar modifications and one or more modified bases.

A modification of a guide sequence can comprise chemically linking to the guide sequence one or more moieties or conjugates that can enhance the activity, cellular distribution or cellular uptake of the guide sequence. These moieties or conjugates can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties include lipid moieties such as a cholesterol moiety, cholic acid, a thioether (e.g., hexyl-S-tritylthiol), a thiocholesterol, an aliphatic chain (e.g., dodecanediol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantane acetic acid, a palmityl moiety, or an octadecylamine or hexylamino-carbonyl-oxycholesterol moiety.

An "artificial target site" or "artificial target sequence" herein refers to a target sequence that has been introduced into the genome of a cell. An artificial target sequence in some embodiments can be identical in sequence to a native target sequence in the genome of the cell, but be located at a different position (a heterologous position) in the genome, or it can different from the native target sequence if located at the same position in the genome of the cell.

An "episome" herein refers to a DNA molecule that can exist in a cell autonomously (can replicate and pass on to daughter cells) apart from the chromosomes of the cell. Episomal DNA can be either native or heterologous to a cell. Examples of native episomes herein include mitochondrial DNA (mtDNA) and chloroplast DNA. Examples of heterologous episomes include plasmids and yeast artificial chromosomes (YACs).

A "protospacer adjacent motif" (PAM) herein refers to a short sequence that is recognized by a nucleic acid-guided endonuclease. The sequence and length of a PAM can differ depending on the Cas protein or Cas protein complex used, but are typically 2, 3, 4, 5, 6, 7, or 8 nucleotides long, for example.

The terms "5'-cap" and "7-methylguanylate (m7G) cap" are used interchangeably herein. A 7-methylguanylate residue is located on the 5' terminus of RNA transcribed by RNA polymerase II (Pol II) in eukaryotes. A capped RNA has a 5'-cap, whereas an uncapped RNA does not have such a cap.

The terminology "uncapped," "not having a 5'-cap," and the like are used interchangeably herein to refer to RNA lacking a 5'-cap and optionally having, for example, a 5'-hydroxyl group instead of a 5'-cap. Uncapped RNA can better accumulate in the nucleus following transcription, since 5'-capped RNA is subject to nuclear export.

The terms "ribozyme," "ribonucleic acid enzyme" and "self-cleaving ribozyme" are used interchangeably herein. A ribozyme refers to one or more RNA sequences that form secondary, tertiary, and/or quaternary structure(s) that can cleave RNA at a specific site, particularly at a cis-site relative to the ribozyme sequence (i.e., auto-catalytic, or self-cleaving). The general nature of ribozyme nucleolytic activity has been described (e.g., Lilley, Biochem. Soc. Trans. 39:641-646). A "HammerHead Ribozyme" (HHR) may comprise a small catalytic RNA motif made up of three base-paired stems and a core of highly conserved, non-complementary nucleotides that are involved in catalysis. Pley et al. (Nature 372:68-74) and Hammann et al. (RNA 18:871-885), which are incorporated herein by reference, disclose hammerhead ribozyme structure and activity. A hammerhead ribozyme may comprise a "minimal hammerhead" sequence as disclosed by Scott et al. (Cell 81:991-1002, incorporated herein by reference), for example.

The terms "targeting," "gene targeting," "DNA targeting," "editing," "gene editing" and "DNA editing" are used interchangeably herein. DNA targeting may be the specific introduction of an indel, knock-out, or knock-in at a particular DNA sequence, such as in a chromosome or episome of a cell. In general, DNA targeting can be performed by cleaving one or both strands at a specific DNA sequence in a cell with a nucleic acid-guided endonuclease associated with a suitable RNA component. Such DNA cleavage, if a double-strand break (DSB), can prompt NHEJ processes which can lead to indel formation at the target site. Also, regardless of whether the cleavage is a single-strand break (SSB) or DSB, HR processes can be prompted if a suitable donor DNA polynucleotide is provided at the DNA nick or cleavage site. Such an HR process can be used to introduce a knock-out or knock-in at the target site, depending on the sequence of the donor DNA polynucleotide. Alternatively, DNA targeting can refer to specific association of a nucleic acid-guided endonuclease/RNA component complex to a target DNA sequence, where the nucleic acid-guided endonuclease does or does not cut a DNA strand (depending on the status of the nucleic acid-guided endonuclease's endonucleolytic domains).

The term "indel" refers to an insertion or deletion of a nucleotide base or bases in a target DNA sequence in a chromosome or episome. Such an insertion or deletion may be of 1, 2, 3, 4, 5, 6, 7, 8, 9, 10, or more bases, for example. An indel in certain embodiments can be even larger, at least about 20, 30, 40, 50, 60, 70, 80, 90, or 100 bases. If an indel is introduced within an open reading frame (ORF) of a gene, oftentimes the indel disrupts wild type expression of protein encoded by the ORF by creating a frameshift mutation.

The terms "knock-out," "gene knock-out" and "genetic knock-out" are used interchangeably herein. A knock-out represents a DNA sequence of a cell that has been rendered partially or completely inoperative by targeting with a nucleic acid-guided endonuclease; such a DNA sequence prior to knock-out could have encoded an amino acid sequence, or could have had a regulatory function (e.g., promoter), for example. A knock-out may be produced by an indel (by NHEJ, prompted by Cas-mediated cleavage), or by specific removal of sequence (by HR, prompted by Cas-mediated cleavage or nicking, when a suitable donor DNA polynucleotide is also used), that reduces or completely destroys the function of sequence at, adjoining, or near the targeting site. A knocked out DNA polynucleotide sequence can alternatively be characterized as being partially or totally disrupted or downregulated, for example.

The terms "knock-in," "gene knock-in" and "genetic knock-in" are used interchangeably herein. A knock-in represents the replacement or insertion of a DNA sequence at a specific DNA sequence in a cell by targeting with a nucleic acid-guided endonuclease (by HR, prompted by nucleic acid-guided endonuclease-mediated cleavage or nicking, when a suitable donor DNA polynucleotide is also used). Examples of knock-ins are a specific insertion of a heterologous amino acid coding sequence in a coding region of a gene, or a specific insertion of a transcriptional regulatory element in a genetic locus. The terms "donor polynucleotide," "donor DNA," "targeting polynucleotide" and "targeting DNA" are used interchangeably herein. A donor polynucleotide refers to a DNA sequence that comprises at least one sequence that is homologous to a sequence at or near a DNA target site (e.g., a sequence specifically targeted by a Cas protein). A suitable donor polynucleotide is able to undergo HR with a DNA target site if the target site contains a SSB or DSB (such as can be introduced using certain Cas proteins associated with an appropriate RNA component). A "homologous sequence" within a donor polynucleotide can, for example, comprise or consist of a sequence of at least about 25 nucleotides, for example, having 100% identity with a sequence at or near a target site, or at least about 90%, 91%, 92%, 93%, 94%, 95%, 96%, 97%, 98%, or 99% identity with a sequence at or near a target site.

In certain embodiments, a donor DNA polynucleotide can have two homologous sequences separated by a sequence (or base pair) that is heterologous to sequence at a target site. These two homologous sequences of such a donor polynucleotide can be referred to as "homology arms" which flank the heterologous sequence. HR between a target site and a donor polynucleotide with two homology arms typically results in the replacement of a sequence at the target site with the heterologous sequence of the donor polynucleotide (target site sequence located between DNA sequences homologous to the homology arms of the donor polynucleotide is replaced by the heterologous sequence of the donor polynucleotide). In a donor polynucleotide with two homology arms, the arms can be separated by 1 or more nucleotides (i.e., the heterologous sequence in the donor polynucleotide can be at least 1 nucleotide in length). Various HR procedures that can be performed in a cell are disclosed, for example, in DNA Recombination: Methods and Protocols: 1st Edition (H. Tsubouchi, Ed., Springer-Verlag, New York, 2011), which is incorporated herein by reference.

The guide sequence of an RNA component (e.g., crRNA or gRNA) can be at least 13, 14, 15, 16, 17, 18, 19, 20, 21, 22, 23, 24, 25, 26, 27, 28, 29, or 30 ribonucleotides in length; between 13-30 ribonucleotides in length; between 17-25 ribonucleotides in length; or between 17-20 ribonucleotides in length, for example. In general, a guide sequence has sufficient complementarity with a strand of a target DNA sequence to hybridize with the target sequence and direct sequence-specific binding of a nucleic acid-guided endonuclease or a nucleic acid-guided endonuclease complex to the target sequence (if a suitable PAM is adjacent to the target sequence). The degree of complementarity between a guide sequence and its corresponding DNA target sequence is at least about 90%, 91%, 92%, 93%, 94%, 95%, 96%, 97%, 98%, 99%, or 100%, for example. The guide sequence can be engineered accordingly to target a nucleic acid-guided endonuclease to a DNA target sequence in a cell.

An RNA component can comprise a crRNA, for example, which comprises a guide sequence and a repeat (tracrRNA mate) sequence. The guide sequence is typically located at or near (within 1, 2, 3, 4, 5, 6, 7, 8, 9, 10 or more bases) the 5' end of the crRNA. Downstream of the guide sequence of a crRNA is a "repeat" or "tracrRNA mate" sequence that is complementary to, and can hybridize with, sequence at the 5' end of a tracrRNA. Guide and tracrRNA mate sequences can be immediately adjacent, or separated by 1, 2, 3, 4 or more bases, for example. A tracrRNA mate sequence has, for example, at least 50%, 60%, 70%, 80%, 90%, 95%, 96%, 97%, 98%, 99%, or 100% sequence complementarity to the 5' end of a tracrRNA. In general, degree of complementarity can be with reference to the optimal alignment of the tracrRNA mate sequence and 5' end of the tracrRNA sequence, along the length of the shorter of the two sequences. The length of a tracrRNA mate sequence can be at least 8, 9, 10, 11, 12, 13, 14, 15, 16, 17, or 18 ribonucleotides in length, for example, and hybridizes with sequence of the same or similar length (e.g., plus or minus 1, 2, 3, 4, or 5 bases) at the 5' end of a tracrRNA. Suitable examples of tracrRNA mate sequences comprise (guuuuuguacucucaagauuua)(SEQ ID NO: 21), (guuuuuguacucuca)(SEQ ID NO: 22), (guuuuagagcua)(SEQ ID NO: 23), or (guuuuagagcuag)(SEQ ID NO: 24), or variants thereof that (i) have at least about 90%, 91%, 92%, 93%, 94%, 95%, 96%, 97%, 98%, or 99% sequence identity and (ii) can anneal with the 5'-end sequence of a tracrRNA. The length of a crRNA can be at least about 18, 20, 22, 24, 26, 28, 30, 32, 34, 36, 38, 40, 42, 44, 46, or 48 ribonucleotides; or about 18-48 ribonucleotides; or about 25-50 ribonucleotides, for example.

A tracrRNA can be included along with a crRNA in embodiments in which a Cas9 protein of a type II CRISPR system is comprised in the nucleic acid-guided endonuclease. A tracrRNA comprises in 5'-to-3' direction (i) a sequence that anneals with the repeat region (tracrRNA mate sequence) of crRNA and (ii) a stem loop-containing portion. The length of a sequence of (i) can be the same as, or similar with (e.g., plus or minus 1, 2, 3, 4, or 5 bases), any of the tracrRNA mate sequence lengths disclosed above, for example. The total length of a tracrRNA (i.e., sequence components (i) and (ii)) can be at least about 30, 35, 40, 45, 50, 55, 60, 65, 70, 75, 80, 85, or 90 (or any integer between 30 and 90) ribonucleotides, for example. A tracrRNA may further include 1, 2, 3, 4, 5, or more uracil residues at the 3'-end, which may be present by virtue of expressing the tracrRNA with a transcription terminator sequence.

A tracrRNA can be derived from any of the bacterial species listed above from which a Cas9 sequence can be derived, for example. Examples of suitable tracrRNA sequences include those disclosed in U.S. Pat. No. 8,697,359 and Chylinski et al. (RNA Biology 10:726-737), which are incorporated herein by reference. A preferred tracrRNA can be derived from a *Streptococcus* species tracrRNA (e.g., *S. pyogenes, S. thermophilus*). Other suitable examples of tracrRNAs may comprise: uagcaaguuaaaauaaggcuaguccguuaucaacuugaaaaaguggcaccgagucggugc (SEQ ID NO: 25), uagcaaguuaaaauaaggcuaguccguuaucaacuugaaaaagug (SEQ ID NO: 26), or uagcaaguuaaaauaaggcuaguccguuauca (SEQ ID NO: 27), which are derived from *S. pyogenes* tracrRNA. Other suitable examples of tracrRNAs may comprise: uaaaucuugcagaagcuacaaagauaaggcuucaugccgaaaucaacacccugucauuuuauggcagggguguuuucguuauu uaa (SEQ ID NO: 28), ugcagaagcuacaaagauaaggcuucaugccgaaaucaacacccugucauuuuauggcagggguguuuucguuauuua (SEQ ID NO: 29), or ugcagaagcuacaaagauaaggcuucaugccgaaaucaacacccugucauuuuauggcagggugu (SEQ ID NO: 30), which are derived from *S. thermophilus* tracrRNA.

Still other examples of tracrRNAs are variants of these tracrRNAs that (i) have at least about 80%, 85%, 90, 91, 92, 93, 94, 95, 96, 97, 98, or 99% sequence identity therewith and (ii) can function as a tracrRNA (e.g., 5'-end sequence can anneal to tracrRNA mate sequence of a crRNA, sequence downstream from the 5'-end sequence can form one or more hairpins, variant tracrRNA can form a complex with a nucleic acid-guided endonuclease).

An RNA component of a nucleic acid-guided endonuclease disclosed herein (e.g., an RNA component that may be associated with a nucleic acid-guided endonuclease component) can comprise, for example, a guide RNA (gRNA) comprising a crRNA operably linked to, or fused to, a tracrRNA. The crRNA component of a gRNA in certain preferred embodiments is upstream of the tracrRNA component (i.e., such a gRNA comprises, in 5'-to-3' direction, a crRNA operably linked to a tracrRNA). Any crRNA and/or tracrRNA (and/or portion thereof, such as a crRNA repeat sequence, tracrRNA mate sequence, or tracrRNA 5'-end sequence) as disclosed herein (e.g., above embodiments) can be comprised in a gRNA, for example.

The tracrRNA mate sequence of the crRNA component of a gRNA should be able to anneal with the 5'-end of the tracrRNA component, thereby forming a hairpin structure. Any of the above disclosures regarding lengths of, and percent complementarity between, tracrRNA mate sequences (of crRNA component) and 5'-end sequences (of tracrRNA component) can characterize the crRNA and tracrRNA components of a gRNA, for example. To facilitate this annealing, the operable linkage or fusion of the crRNA and tracrRNA components preferably comprises a suitable loop-forming ribonucleotide sequence (i.e., a loop-forming sequence may link the crRNA and tracrRNA components together, forming the gRNA). Suitable examples of RNA loop-forming sequences include GAAA, CAAA and AAAG. However, longer or shorter loop sequences may be used, as may alternative loop sequences. A loop sequence preferably comprises a ribonucleotide triplet (e.g., AAA) and an additional ribonucleotide (e.g., C or G) at either end of the triplet.

A gRNA forms a hairpin ("first hairpin") with annealing of its tracrRNA mate sequence (of the crRNA component) and tracrRNA 5'-end sequence portions. One or more (e.g., 1, 2, 3, or 4) additional hairpin structures can form downstream from this first hairpin, depending on the sequence of the tracrRNA component of the gRNA. A gRNA may therefore have up to five hairpin structures, for example. A gRNA may further include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more residues following the end of the gRNA sequence, which may be present by virtue of expressing the gRNA with a transcription terminator sequence, for example. These additional residues can be all U residues, or at least 90%, 91%, 92%, 93%, 94%, 95%, 96%, 97%, 98%, or 99% U residues, for example, depending on the choice of terminator sequence.

No n-limiting examples of suitable gRNAs useful in the disclosed invention are:

```
sgRNA targeting GFP:
GGGCGAGGAGCTGTTCACCG sgRNAs targeting RIP140:
                                    (SEQ ID NO: 1)
sgRIP140-1:        GGTTTGGAGTCACGTCAGGG (SEQ ID NO: 2)
sgRIP140-2:        GGATTTAAGGTGCTATGGCG (SEQ ID NO: 3)
sgRIP140-3:        GGAGTCGAAGAACATCTGCA (SEQ ID NO: 4)
sgRIP140-4:        GGAGTACTGCAGGCATACGG
```

Other examples of gRNAs include variants of the foregoing gRNAs that (i) have at least about 80%, 85%, 90, 91, 92, 93, 94, 95, 96, 97, 98, or 99% sequence identity (excluding guide sequence in this calculation) with these sequences, and (ii) can function as a gRNA that specifically targets a nucleic acid-guided endonuclease protein to bind with, and optionally nick or cleave, a target DNA sequence.

A gRNA can also be characterized in terms of having a guide sequence (VT domain) followed by a Cas endonuclease recognition (CER) domain A CER domain comprises a tracrRNA mate sequence followed by a tracrRNA sequence.

An RNA component of a nucleic acid-guided endonuclease optionally does not have a 5'-cap (7-methylguanylate (m7G) cap) (i.e., such an RNA component does not have an m7G cap at its 5'-terminus). An RNA component can have, for example, a 5'-hydroxyl group instead of a 5'-cap. Alternatively, an RNA component can have, for example, a 5' phosphate instead of a 5'-cap. It is believed that an RNA component in these embodiments can better accumulate in the nucleus (such as after its transcription in the nucleus, or after its nucleic acid-guided endonuclease-mediated import into the nucleus, depending on how the RNA component is provided herein), since 5'-capped RNA (i.e., RNA having 5' m7G cap) is subject to nuclear export. Preferred examples of uncapped RNA components include suitable gRNAs, crRNAs, and/or tracrRNAs. In certain embodiments, an RNA component lacks a 5'-cap, and optionally has a 5'-hydroxyl group instead, by virtue of RNA autoprocessing by a ribozyme sequence at the 5'-end of a precursor of the RNA component (i.e., a precursor RNA comprising a ribozyme sequence upstream of an RNA component such as a gRNA undergoes ribozyme-mediated autoprocessing to remove the ribozyme sequence, thereby leaving the downstream RNA component without a 5'-cap). In certain other embodiments, an RNA component herein is not produced by transcription from an RNA polymerase III (Pol III) promoter.

Glucan Particles

In certain embodiments of the invention, complexes comprising a nucleic acid-guided endonuclease, a sequence-specific targeting nucleic acid and/or an amphipathic helical peptide further include a Glucan Particle (GP). For example, complexes comprising a nucleic acid-guided endonuclease, a sequence-specific targeting nucleic acid, and peptide may be encapsulated in a glucan particle to facilitate delivery to a subject. GPs can be made by a variety of methods known in the art. In one embodiment, the process for producing the GPs involves the extraction and purification of the alkali-insoluble glucan particles from the yeast or fungal cell walls. The structure-function properties of the glucan particle preparation depend directly on the source from which it is obtained and also from the purity of the final product. The source of glucan particles can be yeast or other fungi, or any other source containing glucan having the properties described herein. In certain embodiments, yeast cells are a preferred source of glucans. The yeast strains employed in the present process can be any strain of yeast, including, for example, S. cerevisiae, S. delbrueckii, S. rosei, S. microellipsodes, S. carlsbergensis, S. bisporus, S. fermentati, S. rouxii, Schizosaccharomyces pombe, Kluyveromyces polysporus, Candida albicans, C. cloacae, C. tropicalis, C. utilis, Hansenula wingei, H. arni, H. henricii, H. americana, H. canadiensis, H. capsulata, H. polymorpha, Pichia kluyveri, P. pastoris, P. polymorpha, P. rhodanensis, P. ohmeri, Torulopsis bovin, and T. glabrata. Alternatively, mutant yeast strains can be employed.

The yeast cells may be produced by methods known in the art. Typical growth media comprise, for example, glucose, peptone and yeast extract. The yeast cells may be harvested and separated from the growth medium by methods typically applied to separate the biomass from the liquid medium. Such methods typically employ a solid-liquid separation process such as filtration or centrifugation. In the present process, the cells are preferably harvested in the mid- to late logarithmic phase of growth, to minimize the amount of glycogen and chitin in the yeast cells. Glycogen, chitin and protein are undesirable contaminants that affect the biological and hydrodynamic properties of the glucan particles.

Preparation of glucan particles involves treating the yeast with an aqueous alkaline solution at a suitable concentration to solubilize a portion of the yeast and form an alkali-hydroxide insoluble glucan particles having primarily β(1,6) and β(1,3) linkages. The alkali generally employed is an alkali-metal hydroxide, such as sodium or potassium hydroxide or an equivalent. The starting material can comprise yeast separated from the growth medium.

The treating step is performed by extracting the yeast in the aqueous hydroxide solution. The intracellular components and, optionally, the mannan portion, of the cell are solubilized in the aqueous hydroxide solution, leaving insoluble cell wall material which is substantially devoid of protein and having substantially unaltered β(1,6) and β(1,3) linked glucan. The intracellular constituents are hydrolyzed and released into the soluble phase. The conditions of digestion are such that at least in a major portion of the cells, the three dimensional matrix structure of the cell walls is not destroyed. In particular circumstances, substantially all the cell wall glucan remains unaltered and intact.

In certain embodiments, the aqueous hydroxide digestion step is carried out in a hydroxide solution having initial normality of from about 0.1 to about 10.0. A preferred aqueous hydroxide solution is sodium hydroxide. The digestion can be carried out at a temperature of from about 20° C. to about 121° C., for example, at about 70° C. to about 100° C. with lower temperatures requiring longer digestion times. When sodium hydroxide is used as the aqueous hydroxide, the temperature can be about 70° C., 80° C., 90° C. or about 100° C. and the solution has an initial normality of from about 0.75 to about 1.5.

Generally from about 10 to about 500 grams of dry yeast per liter of hydroxide solution is used. In certain embodiments, the aqueous hydroxide digestion step is carried out by a series of contacting steps so that the amount of residual contaminants such as proteins are less than if only one contacting step is utilized. In certain embodiments, it is desirable to remove substantially amounts of protein material from the cell. Additional extraction steps are preferably carried out in a mild acid solution having a pH of from about 2.0 to about 6.0. Typical mild acid solutions include hydrochloric acid, sodium chloride adjusted to the required pH with hydrochloric acid and acetate buffers. Other typical mild acid solutions are in sulfuric acid and acetic acid in a suitable buffer. This extraction step is preferably carried out at a temperature of from about 20° C. to about 100° C. The digested glucan particles can be, if necessary or desired, subjected to further washings and extraction to reduce the protein and contaminant levels. After processing the product pH can be adjusted to a range of about 6.0 to about 7.8.

The glucan particles can be further processed and/or further purified, as desired. For example, the glucan can be dried to a fine powder (e.g., by drying in an oven); or can be treated with organic solvents (e.g., alcohols, ether, acetone, methyl ethyl ketone, chloroform) to remove any traces or organic-soluble material, or retreated with hydroxide solution, to remove additional proteins or other impurities that may be present.

In exemplary methods, about 100 g of yeast, e.g., Baker's yeast, are suspended in about 1 L 1M NaOH and heated to about 80° C. for about 1 hour. Following centrifugation, the insoluble material is suspended in about 1 L of water and the pH adjusted to about 4-5 with HCl and incubated at about 55° C. for about 1 hour. Water and solvent washes can be carried out about 1 to 5 times.

An alternative approach utilizes fewer components for encapsulating the desired therapeutic payload, e.g., a nucleic acid-guided endonuclease and/or a sequence-specific targeting nucleic acid sequence. Components include glucan shells loaded with complexes of a nucleic acid-guided endonuclease and/or a sequence-specific targeting nucleic acid sequence and, for example, an amphipathic delivery peptide (e.g., Endo-Porter), which facilitates transport of a nucleic acid-guided endonuclease and/or a sequence-specific targeting nucleic acid sequence into cells (see e.g., Tesz et al. *Biochem. J.* (2011) 436, 351-362).

Methods of Targeting RIP140

RIP140 is a nuclear protein containing approximately 1158 amino acids, with a size of approximately 128 kDa. RIP140 binds to nuclear receptors via LXXLL motifs, wherein L is leucine and X is any amino acid (Heery et al., Nature, 387(6634):733-6, 1997). Ten LXXLL motifs are found in the RIP140 sequence. RIP140 also interacts with histone deacetylases and with C-terminal binding protein (CTBP) via a PXDLS motif found in the RIP140 sequence.

A human RIP140 nucleotide sequence is listed in GenBank® under Accession No. NM-003489. The corresponding human amino acid sequence is found under Accession No. NP-003480. The nucleotide sequence of the chromosomal region containing the entire human RIP140 gene can be found in GenBank® under Accession No. AF248484. A murine RIP140 nucleotide sequence can be found in GenBank® under Accession No. NM-173440. The corresponding murine amino acid sequence is found under Accession No. NP 775616. RIP140 is highly conserved between vertebrate species.

A number of RIP140 homologs are known in the art, and are listed in GenBank®. Inhibition of expression of a RIP140 in a cell that normally conducts glucose transport in response to stimulation by insulin (e.g., a fat cell) results in increased glucose transport. A biologically active RIP140 or fragment thereof includes sequences that can be transfected into a RIP140−/− cell and restore RIP140 activity.

In certain embodiments of the invention, a nucleic acid-guided endonuclease-sequence-specific targeting nucleic acid-amphipathic peptide complex (e.g., a Cas9-gRNA-Endo-Porter complex) is delivered to a cell expressing RIP140, e.g., a fat cell (e.g., a white fat cell, a beige fat cell, a brown fat cell, an adipocyte, a pre-adipocyte or the like) using methods described herein or known in the art. The amphipathic peptide (e.g., Endo-Porter peptide) portion of the complex mediates delivery of the complex into the fat cell. After delivery of the complex into the fat cell, the sequence-specific targeting nucleic acid (e.g., gRNA) directs delivery of the nucleic acid-guided endonuclease (e.g., Cas 9) to the target nucleic acid sequence (e.g., gene) in the fat cell (e.g., RIP140). The nucleic acid-guided endonuclease (e.g., Cas 9) can then mediate editing or deletion of the target nucleic acid sequence (e.g., gene) in the fat cell.

Nucleic acid sequences that target RIP140, e.g., gRNAs are described herein. Exemplary gRNAs that target RIP140 are:

```
                                         (SEQ ID NO: 1)
    sgRIP140-1:      GGTTTGGAGTCACGTCAGGG (SEQ ID NO: 2)
    sgRIP140-2:      GGATTTAAGGTGCTATGGCG
``` sgRIP140-3:    GGAGTCGAAGAACATCTGCA (SEQ ID NO: 3)

sgRIP140-4:    GGAGTACTGCAGGCATACGG. (SEQ ID NO: 4)

In certain embodiments, a fat cell is contacted with a complex of the invention in vitro (e.g., in tissue culture). In other embodiments, a fat cell is contacted with a complex of the invention in vivo (e.g., by injection directly into fat tissue or into fat-adjacent muscle tissue). In other embodiments, a fat cell that has been contacted with a complex of the invention in vitro is administered to a fat cell in vivo using the methods described herein or known in the art (e.g., by injection directly into fat tissue or into fat-adjacent muscle tissue).

Compounds (e.g., nucleic acid-guided endonuclease-sequence-specific targeting nucleic acid-amphipathic peptide complexes (e.g., Cas9-gRNA-Endo-Porter complexes)) can be tested for their ability to target RIP140 by assaying modulation of one or more RIP140-mediated activities. For example, compounds that target RIP140 and inhibit RIP140 activity result in at least one of increased insulin sensitivity, increased glucose transport, increased energy expenditure, increased metabolism, increased brown fat formation, increased beige fat formation and/or increased fatty acid oxidation. Methods of assaying a compound for such activities are known in the art.

In one embodiment, a cell-based assay is employed in which a cell that expresses RIP140 is contacted with a complex described herein. The ability of the complex to inhibit RIP140 expression or activity is then determined, e.g., by monitoring, glucose transport, insulin sensitivity, increased energy expenditure, increased metabolism, increased brown fat formation, increased beige fat formation or increased fatty acid oxidation. The cell, for example, can be a yeast cell or a cell of mammalian origin, e.g., rat, mouse, or human. In particular embodiments, the cell is an adipose cell, e.g., a pre-adipocyte, an adipocyte, a white fat cell, a beige fat cell, a brown fat cell and the like.

In one embodiment, a C57Bl/6 mouse model of high fat diet feeding to induce obesity, insulin resistance and type 2 diabetes can be used. This diet/model produces the following characteristics of obesity: significant weight gain due to adipose tissue expansion impaired glucose tolerance and insulin responsiveness in C57Bl/6 male mice. The high fat diet (60% calories from fat) model is a widely used, standardized and highly reproducible model, and is considered a relevant model to dietary obesity in humans.

In another embodiment, a NOD/scid IL-6Rgamma null (NSG mouse) model can be used. These mice lack mature T cells, B cells, or functional NK cells, and are deficient in cytokine signaling, leading to better engraftment of human as well as non-congenic mouse cells. They have been widely employed for functional assays of human cells in the complex in vivo environment. Although these mice are resistant to diet-induced obesity, housing under thermoneutral conditions enhances this property and leads to insulin resistance.

In another embodiment, discarded adipose tissue from individuals that consented at a pre-operative visit prior to panniculectomy, and who have had bariatric surgery at any time prior to panniculectomy, will be used.

In another embodiment, inhibitors of RIP140 (gene, RNA and/or protein) are identified. For example, a cell or cell-free mixture is contacted with a complex described herein and the expression of RIP140 gene, mRNA and/or protein evaluated relative to the level of expression of RIP140 gene, mRNA and/or protein in the absence of the complex. When expression of RIP140 mRNA or protein is less (statistically significantly less) in the presence of the complex than in its absence, the complex is identified as an inhibitor of RIP140 gene, mRNA and/or protein expression. The level of RIP140 gene, mRNA and/or protein expression can be determined by methods described herein and methods known in the art such as Southern blot, Northern blot or Western blot for detecting RIP140 gene, mRNA or protein, respectively.

In another aspect, the new methods described herein pertain to a combination of two or more of the assays described herein. For example, a complex can be identified using a cell-based or a cell-free assay, and the ability of the agent to modulate the activity of a RIP140 protein can be confirmed in vivo, e.g., in an animal such as an animal model for obesity or diabetes (e.g., type II diabetes, e.g., ob/ob mice, db/db mice; see, e.g., Sima A A F, Shafrir E. Animal Models in Diabetes: A Primer. Taylor and Francis, Publ Amsterdam, Netherlands, 2000).

This invention further pertains to novel complexes identified by the above-described screening assays. Accordingly, it is within the scope of this invention to further use a complex identified as described herein (e.g., a RIP140 inhibiting complex) in an appropriate animal model to determine the efficacy, toxicity, side effects, or mechanism of action, of treatment with such an agent. Furthermore, novel complexes identified by the above-described screening assays can be used for treatments as described herein.

Complexes that inhibit RIP140 can be tested for their ability to affect metabolic effects associated with RIP140 using methods known in the art and methods described herein. For example, the ability of a complex to modulate glucose transport (in the presence or absence of insulin) can be tested using an assay for 2-deoxyglucose uptake as described in Frost and Lane (J. Biol. Chem., 260:2646-2652, 1985) and glucose conversion to glyceride fatty acids can be assayed as described in DiGirolamo et al. (J. Lipid Res., 15:332-338, 1974). The conversion of white fat to brown fat can be monitored as described by Tiraby et al. (J. Biol. Chem., 278:33370-33376, 2003), e.g., by assaying UCP1 (uncoupling protein 1). An increase in the amount of UCP1 or other indicator of brown fat metabolism indicates that RIP140 expression or activity in inhibited.

Pharmaceutical Compositions

A complex that has been screened by a method described herein and determined to inhibit RIP140 can be considered a candidate complex. A candidate complex that has been screened, e.g., in an in vivo model of a diabetes or obesity, and determined to have a desirable effect on the disorder, e.g., by increasing glucose transport, reducing glucose levels in vivo, increasing brown fat, increasing beige fat, decreasing white fat, and/or reducing insulin levels, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions.

The complexes described herein that can inhibit RIP140 can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

Toxicity and therapeutic efficacy of such compounds can be determined known pharmaceutical procedures in cell cultures (e.g., in cultures of fat cells, muscle cells, or liver cells) or experimental animals (animal models of obesity or of diabetes (e.g., type II diabetes). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating diabetes in a subject), the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans Levels in plasma may be measured, for example, by high performance liquid chromatography.

Exemplary doses of complex include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these complexes are to be administered to an animal (e.g., a human) to inhibit RIP140, a physician, veterinarian, or researcher may, for example, prescribe a relatively low dose at first, subsequently increasing the dose until an appropriate response is obtained (e.g., an appropriate blood glucose level). In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

Methods of Treatment

Complexes described herein and those identified as described herein can be used to treat a subject that is at risk for or has a glucose transport-related disorder such as type II diabetes, prediabetes and/or gestational diabetes. Methods of identifying such individuals are known in the art. Thus, methods and compositions for both prophylactic and therapeutic methods of treating a subject at risk of (or susceptible to) a disorder or having a disorder associated with aberrant or unwanted RIP140 expression or activity are described herein. As used herein, the term "treatment" is defined as the application or administration of a therapeutic compound to a patient, or application or administration of a therapeutic compound to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic compound includes, but is not limited to, nucleic acid-guided endonuclease-sequence-specific targeting nucleic acid-amphipathic peptide complexes (e.g., Cas9-gRNA-Endo-Porter complexes) that target RIP140 for gene editing and/or deletion.

Provided herein are methods for preventing in a subject (e.g., a human), a disease or condition associated with an aberrant or unwanted RIP140 expression or activity, by administering to the subject a nucleic acid-guided endonuclease-sequence-specific targeting nucleic acid-amphipathic peptide complex (e.g., a Cas9-gRNA-Endo-Porter complex) to target RIP140 for gene editing and/or deletion. Subjects at risk for a disease that is caused or contributed to by aberrant or unwanted RIP140 expression or activity can be identified by, for example, any or a combination of diagnostic or prognostic assays as described herein. Administration of a prophylactic compound can occur prior to the manifestation of symptoms characteristic of full-blown disease, e.g., a subject exhibiting hyperglycemia or prediabetes but that does not exhibit effects of diabetes associated with advanced disease, such that the disease or disorder is prevented or, alternatively, delayed in its progression. Methods known in the art can be used to determine the efficacy of the treatment. The appropriate compound used for treating the subject can be determined based on screening assays described herein.

As discussed, successful treatment of glucose transport-related disorders can be brought about by techniques that serve to inhibit the expression or activity of target gene products. For example, a nucleic acid-guided endonuclease-sequence-specific targeting nucleic acid-amphipathic peptide complex (e.g., a Cas9-gRNA-Endo-Porter complex) that targets RIP140 for gene editing and/or deletion, e.g., an agent identified using one or more of the assays described above, can be used as described herein to prevent and/or ameliorate symptoms of glucose transport-related disorders.

The identified complexes that inhibit RIP140 gene expression, synthesis and/or activity can be administered to a patient at therapeutically effective doses to prevent, treat, or ameliorate RIP140-associated disorders (e.g., type II diabetes, prediabetes and gestational diabetes). A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies generally within a range of circulating concentrations that include the ED50 with little or no toxicity. The dosage can vary within this range depending upon the dosage form employed and the route of administration utilized. For any compound used as described herein, the therapeutically effective dose can be estimated initially from cell culture assays. A dose can be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans Levels in plasma can be measured, for example, by high performance liquid chromatography.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

Example 1

Preparation of gRNA Template and Synthesis of gRNA

Guide RNA (gRNA) sequences were designed using sgRNA Designer developed by The Broad Institute (Doench et al., Nat Biotech, 34: 184-191, 2016). Templates for gRNAs were generated by inserting annealed complementary oligonucleotides with the gRNA sequences to the pUC57-sgRNA expression vector encoding a T7 promoter. The gRNA templates were linearized by Dra I and transcribed in vitro using the MEGAshortscript T7 Transcription Kit according to manufacturer's instruction. Transcribed gRNA was resolved on a 10% denaturing urea-PAGE gel to check the size and purity.

Example 2

Preparation of CRISPR-Based Delivery Particles (CriPs)

The CRISPR-based nanoparticles (CriPs) targeting RIP140 were synthesized as shown in FIG. 1. Briefly, Cas9 was purified from *E. coli* and incubated with gRNA for 10 minutes at 37° C. in a Buffer 3 with BSA (100 μg/mL BSA, 100 mM NaCl, 50 mM Tris-HCl, 10 mM $MgCl_2$, and 1 mM DTT). Alternative buffers that are suitable for this reaction include PBS, OptiMEM I reduced serum media, Buffer 3 without BSA (100 mM NaCl, 50 mM Tris-HCl, 10 mM $MgCl_2$, 1 mM DTT, pH 7.9) and Cas9 Dilution Buffer (20 mM HEPES, pH 7.5, 150 mM KCl, 1% sucrose). The Cas9-gRNA complex was then incubated with an amphipathic peptide, Endo-Porter, for 15 minutes at room temperature in PBS, pH 7.4 to form the final CRISPR delivery particles (CriPs).

Example 3

GFP Deletion in J774 Macrophages by Treatment with CriPs

GFP expressing J774 cells were plated in 12 well plates with $1 \times 10^5$ cells per well overnight. Cells were either untreated or treated with CriPs—EP coated Cas9/sgRNA complexes with sgRNA sequence targeting GFP (sgGFP) or a control sequence (sgCONTROL). 24 hours later, CriPs were replaced with fresh culture media. At day 5 post treatment, FACS analysis was performed to measure the loss of GFP. FIG. 2 shows GFP-targeting CriPs led to a 41.1% indels in the genomic DNA of GFP-expressing J774 cells. FIG. 3 shows that treatment of GFP-expressing J774 cells with GFP-targeting CriPs resulted in a 55.2% loss of GFP.

Example 4

GFP Deletion in Primary Pre-Adipocytes by Treatment with CriPs

In order to determine the efficacy of delivery of CRISPR-based nanoparticles (CriPs) CriPs targeting GFP were synthesized as discussed in Example 2. Pre-adipocytes (progenitor cells) were isolated from transgenic GFP mice and seeded in a 12 well plate at $8 \times 10^4$ cells per well and grown in cell culture media overnight. The GFP expressing cells were then treated with GFP-CriPs (EP-Cas9-sgGFP) and control-CriPs (EP-Cas9-sgCONTROL) for 24 hours at which point CriPs were removed and replaced with fresh cell culture media. At day 5, FACS analysis was performed to measure the loss of GFP in the pre-adipocytes. FIG. 4 shows that treatment of GFP-expressing pre-adipocytes in vitro with GFP targeting CriPs resulted in a 48.5% loss of GFP compared to control CriPs.

Example 5

RIP140 Deletion in Adipocytes by Treatment with CriPs

Figure 5A:
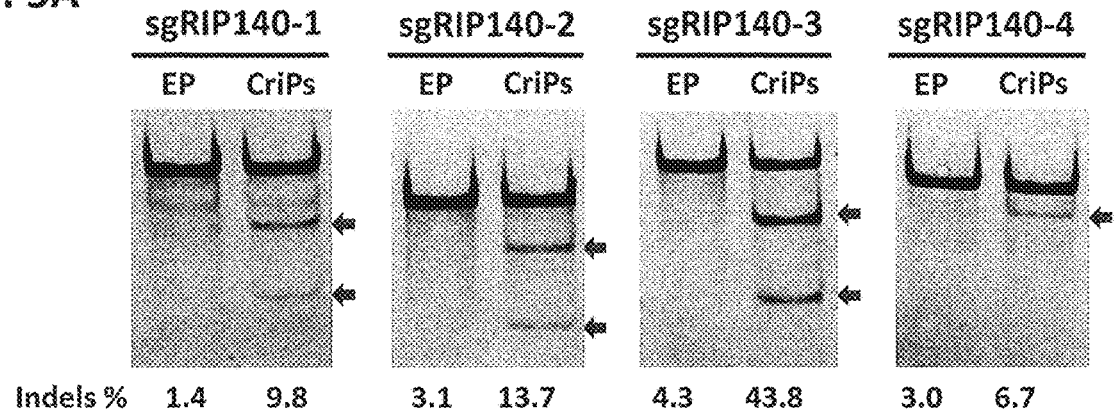
FIG. 5A-FIG. 5B show that RIP140 deletion by treatment with RIP140-targeting CriPs in adipocytes increased the expression of UCP1 45-fold. Four different gRNAs targeting RIP140 (sgRIP140-1, sgRIP140-2, sgRIP140-3, sgRIP140-4) were synthesized by in vitro T7 transcription and complexed with Cas9 protein to form the Cas9/sgRNA complexes. Primary pre-adipocytes were treated with CriPs targeting RIP140 as well as control groups (EP-Cas9/sgGFP, EP-Cas9 only, EP only, non-treated). After 24 hours, CriPs were replaced by fresh culture media. Once the pre-adipocytes reached 100% confluence, the cells were differentiated to form adipocytes. At day 8 of differentiation, cells were collected to measure RIP140 deletion and UCP1 expression. Cas9-sgRNA: 100 nM, EP: 25 µM.
Figure 5B:
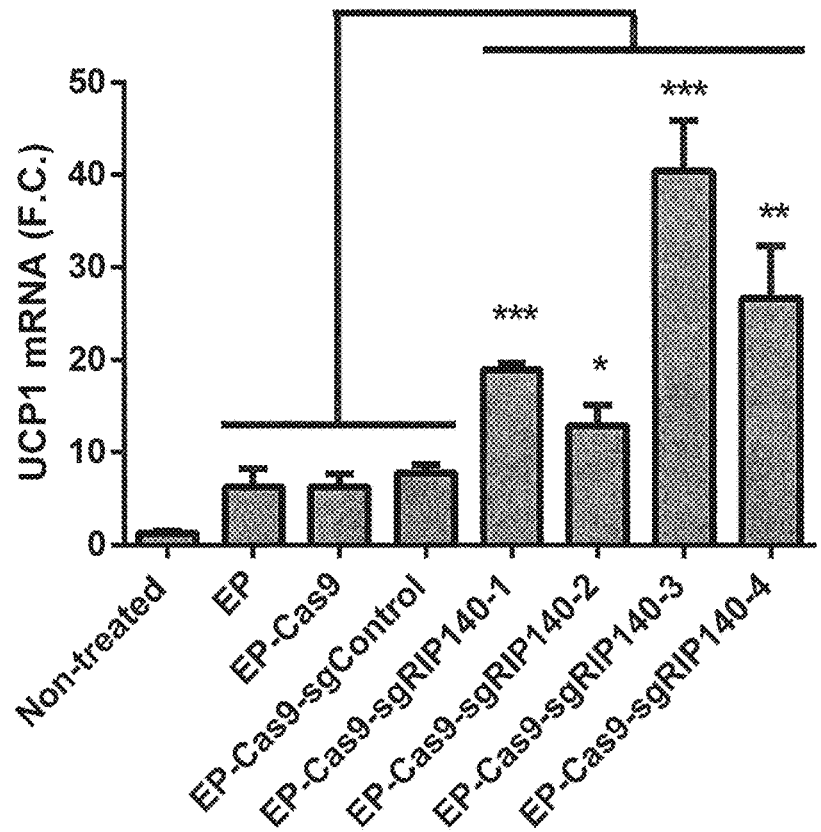

In order to determine the efficacy of CRISPR-based nanoparticles in deleting RIP140, CriPs targeting RIP 140 were synthesized with 4 different gRNAs targeting RIP140 (sgRIP140-1, sgRIP140-2, sgRIP140-3, sgRIP140-4) as discussed in Example 1. Pre-adipocytes were isolated from wild-type mice and seeded in a 12 well plate at $8 \times 10^4$ cells per well and grown in cell culture media overnight. The cells were then treated with RIP140-CriPs (EP-Cas9/sgRIP140-1, 2, 3, 4) or control CriPs (EP-Cas9/sgRIP140-1, 2, 3, 4 control) for 24 hours at which point the CriPs were removed and replaced with fresh cell culture media. When the pre-adipocytes reached 100% confluence the progenitors were differentiated into mature adipocytes. At day 8 of differentiation, the adipocytes were harvested to measure RIP140 deletion and UCP1 expression. RIP140 is a repressor of UCP1; therefore decreased RIP140 should result in increased UPC1 expression in adipocytes (Steel et al., *J Endocrinol*, 185: 1-9, 2005; Puri, et al., *J Lipid Res*, 48: 465-71, 2007). Quantitative RT-PCR analysis of UPC1 expression shows that adipocytes treated with CriPs targeting RIP140 led to increased expression of UPC1 mRNA (FIG. 5B). A T7E1 assay was performed to determine if there was gene editing in RIP140 genomic DNA in CriPs treated adipocytes. FIG. 5A shows that all 4 RIP140-CriPs caused gene editing in RIP140 genomic DNA, where no gene editing of RIP140 occurred with the control CriPs.

White adipocytes treated with CriPs loaded with sgRIP140 sequence #3 (sgRIP140-3) showed the highest indels percentage in the RIP140 genomic locus and the highest increase in UCP1 expression, indicated by FIG. 5. Primary pre-adipocytes were treated with Cas9-sgRIP140-3-EP and Cas9-sgControl-EP, then differentiated to mature white adipocytes. The expression of thermogenic genes, inflammatory genes and neurotropic factors were measured by RT-PCR. The thermogenic genes (UCP1, CIDEA, PGC1α, PRDM16, CPT1b) were increased with the treatment of CriPs loaded with sgRIP140-3, compared to the control group (FIG. 6B). Neurotropic factors (NRG4, NNAT, NRN1) were also increased with the treatment of CriPs-sgRIP140-3 (FIG. 6D). Inflammatory genes (IL1β, IL4, IL6, IL10, MCP1) were not changed between CriPs-sgRIP140 and CriPs-sgControl groups (FIG. 6C).

Example 6

GFP Deletion in GFP Transgenic Mice by Treatment with CriPs

In order to determine the efficacy of CRISPR-based nanoparticles delivery in vivo, CriPs targeting GFP were synthesized as discussed in Example 1, along with CriPs lacking gRNA as a control. GFP transgenic mice C57BL6-Tg (UBC-GFP) were intraperitoneally injected with GFP CriPs and control CriPs once a day for 5 days. On day 6, the mice were sacrificed and the peritoneal cavity was washed with 5 mL of ice-cold PBS to isolate peritoneal exudate cells (PECs). The PECs were plated in cell culture media (DMEM supplemented with 10% FBS, 100 g/mL streptomycin, 100 units/mL penicillin) overnight to enrich for macrophages. At day 10 (5 days after the last injection), the adherent cells were collected and the loss of GFP was analyzed by FACS analysis. FIG. 9 demonstrates that treatment of intraperitoneal injection of GFP CriPs caused between 2.91-13.9% loss of GFP in macrophages as compared to the control CriPs, which lacked a gRNA.

In order to confirm the deletion of EGFP in EGFP transgenic mice intraperitoneally injected with CriPs-sgEGFP was due to the EGFP genome engineering, PCR amplicons amplified from EGFP genomic DNA were submitted for deep sequencing to study the insertions and deletions (indels). Around 3% of the target sequences were mutated, corroborating with the data of GFP loss measured by flow cytometry shown in FIG. 9. DNA sequences of the EGFP wild-type (WT) and mutants were compared. The mutants included sequences with insertions and deletions of the bases as well as SNPs in the target site (FIG. 10).

Example 7

Monitoring Insertions and Deletions (Indels) by the T7E1 Assay

Cells were lysed in cell lysis buffer (1M KCl, 1M MgCl2, 1M Tris-Base pH 8.3, 0.45% NP40, 0.45% Tween20) and the genomic DNA was used as a template in PCR reactions to amplify the targeted genomic loci. PCR products were purified using QIAquick PCR Purification Kit and quantified by Nanodrop. 200 ng of purified PCR products were mixed with 2 µl of NEBuffer 2 (NEB) in a total volume of 19 µl and denatured then re-annealed with thermocycling at 95° C. for 5 min, 95 to 85° C. at 2° C./s, 85 to 20° C. at 0.2° C./s. The re-annealed DNA was incubated with 1 µl of T7 endonuclease I (T7E1) at 37° C. for 15 min. The reaction was stopped by adding 1.5 µl of 0.25 M EDTA, and analyzed on a 4-20% Mini-Protean TBE Gel electrophoresed for 1.5 hours at 100 V, then stained with ethidium bromide. The percentage of indels was calculated based on the band intensities determined using Image Lab (Bio-Rad). The intensities of the cleaved bands were divided by the total intensities of all bands (uncleaved+cleaved) to determine the % indels to estimate gene modification levels. FIGS. 2 and 5 show T7E1 assays for GFP in J774 cells and RIP140 in adipocytes genomic DNA, respectively.

Figures 7A, 7B:
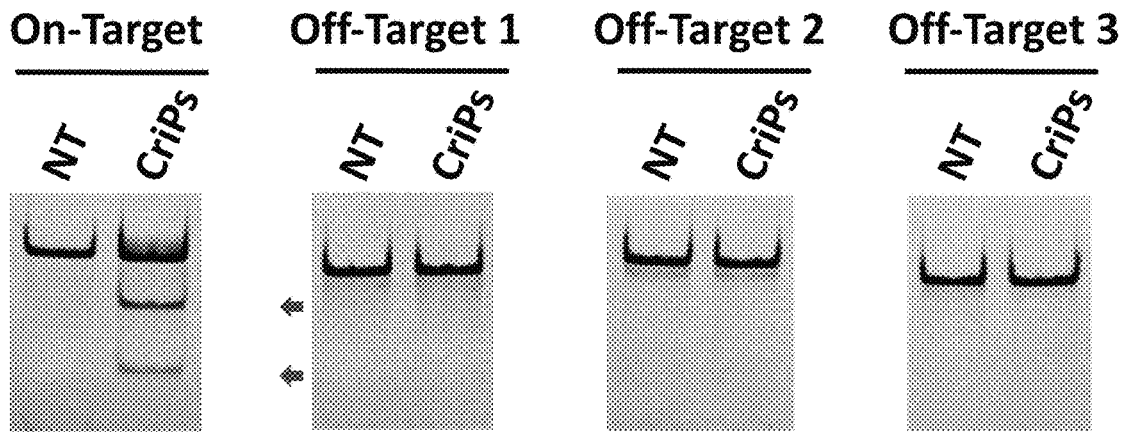
FIG. 7A-FIG. 7B show that Cas9-sgRIP140-3 CriPs did not result in off-target effects as determined by a T7E1 assay. Primary pre-adipocytes were treated with CriPs loaded with sgRIP140-3. Pre-adipocytes were then differentiated to mature white adipocytes. Top off-target candidate sites were determined using the CHOPCHOP program.
Figure 8:
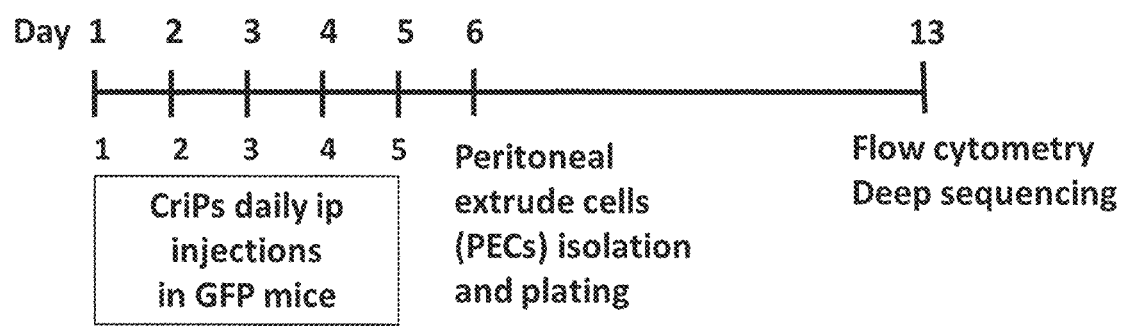
FIG. 8 shows a timeline of i.p. administration of CriPs to EGFP mice. EGFP transgenic mice were i.p. injected daily for 5 days with CriPs targeting EGFP or with a control sequence. On day 6, mice were sacrificed and peritoneal exudate cells (PECs) were collected and plated. At day 13, flow cytometry and deep sequencing were performed to measure the loss of EGFP.

Off-target effects of CriPs targeting RIP140 were determined by the T7E1 assay. Primary pre-adipocytes were treated with CriPs loaded with sgRIP140-3. Top off-target candidate sites were provided by the CHOPCHOP program (FIG. 7B). No sgRIP140-3 off-target effects were observed by the T7E1 assay (FIG. 7A).

Example 8

In Vivo Fat Injection

In order to directly target CriPs to subcutaneous adipose tissue, mice (C57BL/6, male) were anesthetized with a xylasin/ketamine mixture. The intra-subcutaneous (SQ) WAT administration was carried out after a small incision in the skin at the inguinal area. 30 µL samples of CriPs targeting genes of interest as well as control groups were injected into the extracellular fluid around the SQ inguinal fat depot on one side of each mouse. At day 10 post-injection, mice were sacrificed and SQ inguinal fat pads on both sides were collected for histology, T7E1 assay, RT-PCR and Western blot.

Example 9

In Vitro Treatment of Primary GFP Expressing Macrophages (PECs)

In order to assess the efficacy of CriPs in macrophages in vitro, primary GFP expressing peritoneal exudate cells (PECs) were isolated from GFP transgenic mice and plated in 12 well plates with $5 \times 10^5$ cells per well overnight. Cells were treated with CriPs (i.e., EP coated Cas9/sgRNA complexes with sgRNA sequence targeting GFP (sgGFP)) or a control sequence (sgCONTROL). 24 hours later, CriPs were replaced with fresh culture media. At day 5 post treatment, FACS analysis was performed to measure the loss of GFP. 7-AAD staining was used to determine live cells and dead cells. % GFP-shift and % GFP+ was calculated from the live cells. Insertions and deletions (indels) in the GFP genomic locus were measured by T7E1 assay.

Example 10

Adipose Tissue Fat Oxidation as a Target for Treating Type 2 Diabetes

White adipose tissue (WAT) depots that store triglycerides are distributed throughout the body and expand greatly during the onset of obesity. Expansion of the visceral depots of WAT are particularly well correlated with metabolic disease, insulin resistance and development of type 2 diabetes, which occurs when the beta cells of the pancreas are unable to produce enough insulin to overcome insulin resistance and maintain normal fasting levels of glucose. It is unclear exactly how unhealthy expansion of WAT leads to glucose intolerance, but without intending to be bound by scientific theory, a major hypothesis is that lipids that cannot be stored in maximally expanded WAT are ectopically deposited in other tissues, causing insulin resistance. Importantly, it was discovered that humans have another type of adipose tissue, denoted as brown adipose tissue (BAT), containing brown adipocytes that are loaded with mitochondria that can be uncoupled by uncoupling protein UCP-1 to produce heat. Thus BAT is a fat burning tissue in response to catecholamine, as opposed to the fat storing WAT. Furthermore, WAT was found to contain some adipocytes that resemble brown adipocytes and are greatly increased in WAT in response to cold exposure (through catecholamine stimulation). These cells that arise in WAT when humans or mice are cold exposed also express UCP-1 (denoted as "beige" adipocytes) and show high fatty acid oxidation rates.

Figure 13:
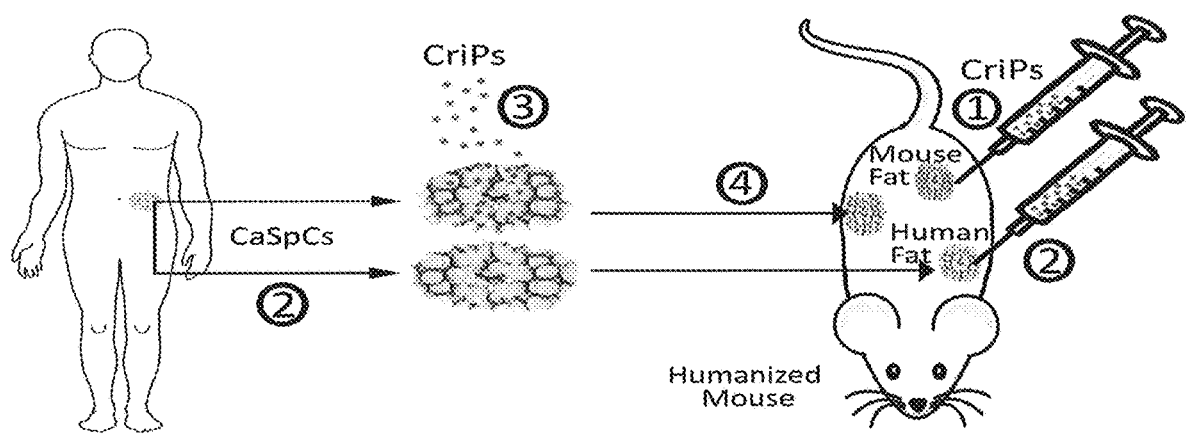
FIG. 13 depicts strategies for using CRISPR-based gene deletion for alleviating type 2 diabetes. CRISPR-based nanoparticles (CriPs) containing Cas9, RIP140-sgRNA, and Endo-Porter peptide, are injected directly into mouse adipose depots (1) or injected into depots of human adipose tissue in "humanized" mice generated from adipocyte progenitor "capillary sprout cells" (CaSpCs) (2), to test therapeutic effects on blood glucose (Strategy A, right side of Figure). In a parallel strategy (Strategy B, left side of Figure), human adipocytes generated from CaSpCs are treated with CriPs ex vivo (3) to delete RIP140, up-regulating UCP-1 and other "fat oxidative" genes, prior to implantation into "humanized" mice (4) to test the effects on glucose tolerance.

Recent data reveal that brown and "beige" adipocytes can favorably control whole body glucose homeostasis and ameliorate diabetes. Several approaches have led to this conclusion including: 1. Lean, healthy human subjects on average harbor much more BAT than obese, glucose intolerant subjects; 2. Selective prevention of the development of "beige" adipocytes in mice (by deletion of a transcription factor) leads to glucose intolerance and diabetes on a high fat diet; 3. Transplantation of brown adipocytes into mice increases glucose tolerance on a high fat diet; 4. Isolation of "beige" adipocytes from human adipose tissue improves glucose tolerance when implanted in "humanized" mice (FIG. 13); 5. Browning of adipose tissue by inducible knockout of fatty acid synthase in adipocytes of adult obese mice improves glucose tolerance; 6. Knockout of UCP-1 in high fat fed mice leads to obesity under thermo-neutral temperatures. These data show that increasing the amount of brown or "beige" adipocytes expressing UCP-1 as well as beneficial factors in mice and humans can improve glucose tolerance and lower blood glucose levels.

Example 11

RIP140 as a Target for Treating Type 2 Diabetes

Figure 11:
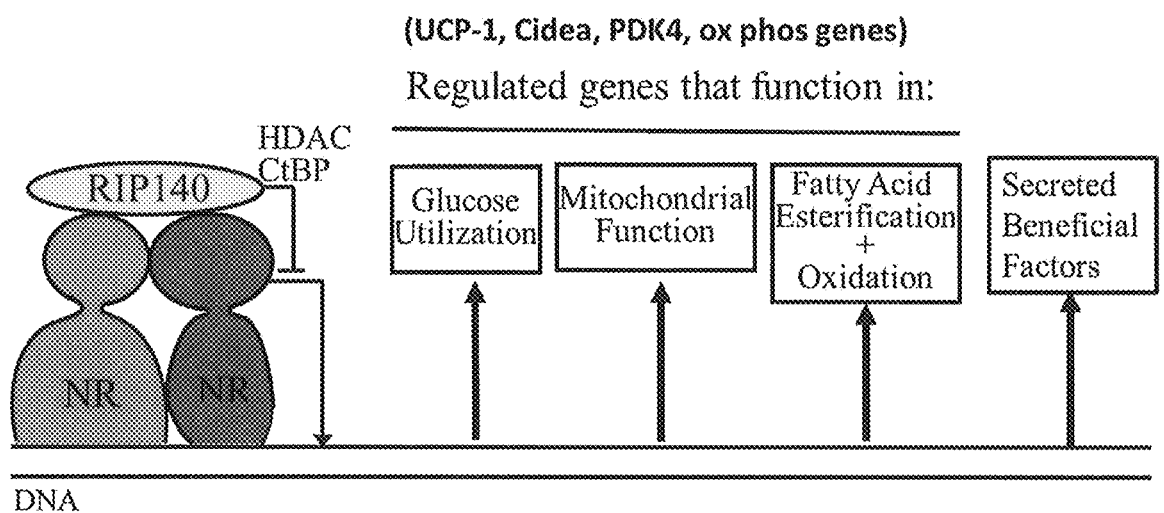
FIG. 11 shows a schematic diagram depicting that RIP140 is a transcriptional corepressor that suppresses genes of glucose and oxidative metabolism.

An important goal in diabetes research is to find molecular targets that suppress fatty acid oxidation and insulin signaling, because inhibiting such targets would enhance these processes. RNAi-based screens have been performed in cultured adipocytes to search for and identify such genes that control insulin sensitivity and energy metabolism. A promising "hit" in these screens of several thousand genes was the nuclear co-repressor Nrip1, termed RIP140. This protein interacts with nuclear receptors (NR, see FIG. 11) to suppress their activity. In adipocytes, RIP140 suppresses the activity of nuclear factors that control the nuclear transcription factor ERRalpha which activates the expression of genes that drive fatty acid and glucose metabolism. Silencing RIP140 by RNAi in adipocytes caused increased expression of Glut4 glucose transporters, many enzymes in fatty acid oxidation and mitochondrial respiration (FIG. 11), including UCP-1, and enhances insulin activation of glucose uptake.

Data showing that RIP140 silencing causes adipose "browning" and enhances insulin action on glucose uptake was verified by whole body and adipose specific knockout in mice, which are lean even on a high fat diet and highly insulin responsive. An effective strategy for targeting RIP140 requires its gene deletion specifically in adipocytes (or muscle) rather than whole body targeting. Therefore, the CRISPR-based complexes directed specifically to adipocytes described herein (i.e., nucleic acid-guided endonuclease-sequence-specific targeting nucleic acid-amphipathic peptide complexes (e.g., Cas9-gRNA-Endo-Porter complexes) that target RIP140 for gene editing and/or deletion) that inhibit RIP140 function by gene deletion rather than direct binding of a small molecule, is a promising therapeutic tool for type 2 diabetes, prediabetes and gestational diabetes.

Example 12

Optimization of RIP140 gRNA Sequences

In order to optimize efficacy of the therapeutic CriPs products described herein (nucleic acid-guided endonuclease-sequence-specific targeting nucleic acid-amphipathic peptide complexes (e.g., Cas9-gRNA-Endo-Porter complexes) that target RIP140 for gene editing and/or deletion), steps to optimize the gene deletion efficacy of RIP140-CriPs are taken by first screening a number of potential sgRNA sequences and selecting the most efficient. This is first done in both mouse and human adipocytes in vitro. Secondly, top mouse sgRNA sequences are further tested in vivo by direct injection into mouse subcutaneous adipose.

As a first approach to optimize RIP140 gRNA efficacy, the sgRNA Designer web tool developed by the Broad Institute (URL: portals.broadinstitute.org/gpp/public/analysis-tools/sgrna-design) is employed. This tool is designed to identify optimum sequences while minimizing potential off-target effects of gRNAs. The top ranked sgRNA sequences for mouse and human RIP140 are selected for screening and further characterization. Selected sgRNA-encoding sequences are synthesized as complementary oligonucleotides (Integrated DNA Technologies, Inc.) with overhanging Bsa1 and Dra1 ends. Templates for sgRNAs are generated by inserting annealed complementary oligonucleotides with the sgRNA sequences to the pUC57-sgRNA expression vector (Addgene) linearized with Bsa1 and Dra1. The pUC57-sgRNA vector encodes a T7 promoter for synthesis of sgRNA via in vitro transcription. The selected gRNAs are incorporated into CriPs, which are used to treat primary mouse adipocytes and human "beige" adipocytes. The efficacy of gene editing is assessed by the T7E1 assay and measurement of RIP140 expression.

Additionally, highly efficient sgRNA species identified in vitro will also be further tested in vivo utilizing direct injections into subcutaneous adipose tissue (SAT) to effect in vivo gene editing, ablation of RIP140 expression, and expression of thermogenic gene programs Mice are treated with CriPs (nucleic acid-guided endonuclease-sequence-specific targeting nucleic acid-amphipathic peptide complexes (e.g., Cas9-gRNA-Endo-Porter complexes) that target RIP140 for gene editing and/or deletion) containing the highly efficient sgRNAs via subcutaneous injection into the WAT. The efficacy of gene editing is assessed by the T7E1 assay and measurement of RIP140 expression.

Example 13

Assessing Efficacy of Metabolic Improvement In Vivo Using Optimized RIP140 gRNA Sequences Human cells differentiated into beige-like cells can be implanted in immune deficient mice, where they can form a viable fat depot, and can improve metabolic parameters in diet-induced obese mice. Similar studies with CriPs-treated human and mouse cells bearing RIP140 deletion are done to assess the efficacy of RIP140 deletion in improving metabolic parameters in obese mice. Male NOD.Cg-PrkdcscidIl2rgtm1Wjl/SzJ (NOD-scid IL2rγnull, NSG) mice, 12-14 weeks of age are obtained from the Jackson Laboratory. Mice are injected subcutaneously with CriPs-treated or control cells suspended in Matrigel. In vivo fat injection is performed as described in Example 8. In order to test the ability of browning brought about by CriP-mediated ablation of RIP140, metabolic assays are performed. For implantation studies, NSG mice which have been implanted with CriPs-treated human or mouse cells will be fed high fat diet starting 11 weeks after implantation. Because NSG mice (which lack a functional immune system) are relatively resistant to HFD-induced obesity, the mice are housed at thermoneutrality (30°) to enhance weight gain and development of insulin resistance. Insulin tolerance tests (ITT) and glucose tolerance tests (GTT) are performed after 4 weeks as a first approximation of metabolic improvements. Selected sgRNA-CriPs combinations that produced robust improvement in ITT and GTT are further characterized by detailed metabolic profiling including euglycemic-hyperinsulinemic clamp studies, measurement of in vivo

Example 14

Targeting CriPs to Adipocytes

Identification of the Adipocyte Specific Aptamers

The composition of CriPs as described in Example 2 is not cell specific; therefore it could potentially target any cell in the body. Aptamers are nucleic acids that take on compact structures through internal nucleotide complementation and can act as ligands or "antibodies" to bind to specific proteins. Recent advances in oligonucleotide medicinal chemistry have enabled design of next generation, fully stabilized small aptamers that are capable of potent, in vivo efficacy at binding cell surface proteins. Large libraries of synthesized aptamers are screened for sequences that bind specifically to adipocytes and no other cell types.

A starting library of potential ssDNA aptamer sequences consisting of 40 random nucleotides flanked by appropriate primer amplification sequences and with attached fluorophore is synthesized. CELL-SELEX assay technology is used to identify the adipocyte specific aptamers. Briefly, the FITC-labeled ssDNA library is denatured at 95° C. for 5 min and then cooled on ice for 10 min to form a secondary structure. The library is then suspended in binding buffer (4.5 g/L glucose, 5 mM MgCl2 and 10% FBS in Dulbecco's PBS) including 0.1 mg/mL salmon sperm DNA to inhibit non-specific binding. Next, the target cells (adipocyte) are incubated with the ssDNA library at 37° C. for 30 min. After centrifugation to pellet cells, the supernatant is removed and the cells are washed five times with 1 mL of binding buffer. The aptamer-bound cells are then enriched using a FACSAria cell sorter (BD Bioscience, San Jose, Calif., USA) to collect FITC-positive cells. Bound ssDNAs are eluted from the collected cells by heating at 95° C. for 5 min. The eluted DNAs are purified by phenol-chloroform extraction, a Sephadex G-25 column purification and ethanol precipitation. The purified ssDNAs are then amplified by PCR with FITC-labeled primers. Selection is repeated for 5 rounds, whereupon deep sequencing is used to determine the complexity of the library and estimate the necessity of further rounds of aptamer testing. Negative selection against mouse primary pre-adipocytes, or human precursor cells prior to induction of differentiation is performed two times after the third and fifth rounds of SELEX, and in further rounds depending on complexity of the library. Finally, selected aptamers are synthesized with FITC fluorophores and specificity is verified by FACS and microscopy of human and mouse cells, as well as microscopy of mouse fat pads. The adipocyte specific aptamers are then conjugated to Endoporter peptide to enhance CriP targeting to adipocytes.

Binding of the Aptamers to CriPs

Figure 12:
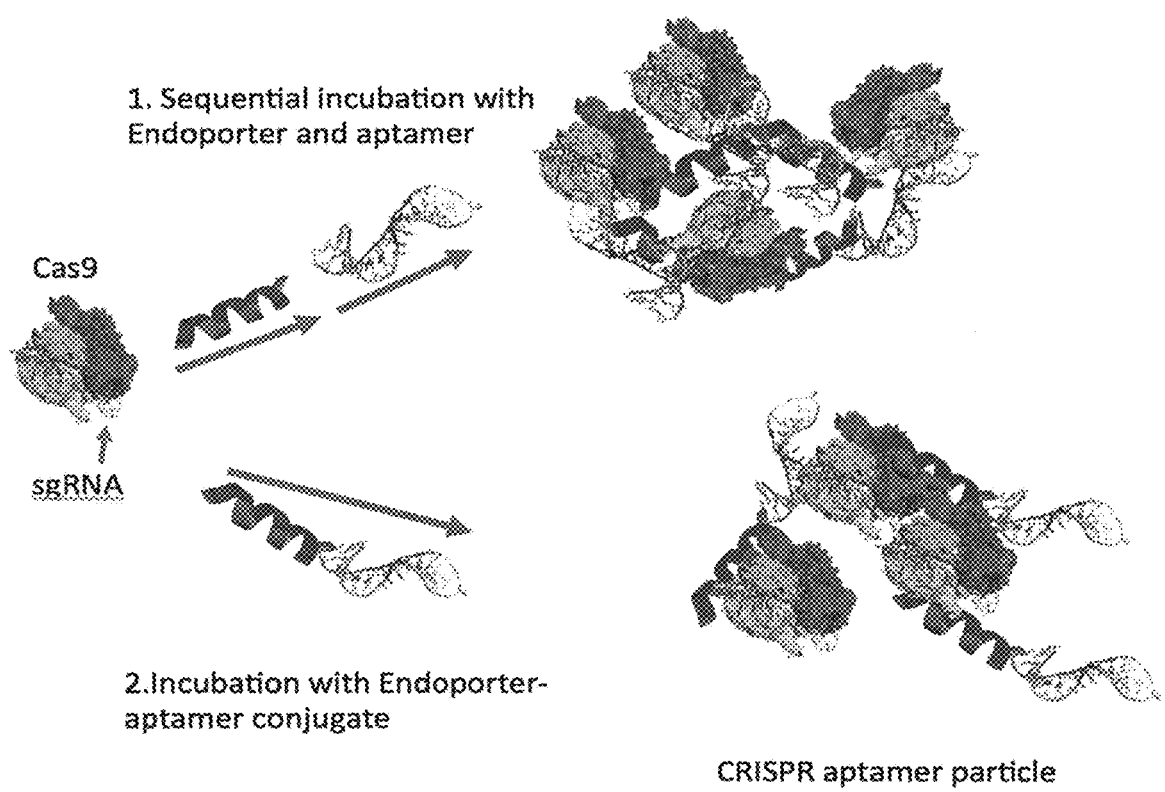
FIG. 12 shows strategies for incorporation of aptamers into CriPs complexes. In one approach, aptamer-CriPs are formed as depicted in FIG. 1 then incubated with aptamers. In a second approach, Endoporter is incubated with the aptamer prior to CriP formation.

Endo-Porter has a propensity to interact with nucleic acid phosphate backbones by means of ionic interaction. Thus, in a first approach to bind aptamers to CriPs, CriPs generated as described in Example 2 are further incubated with aptamer (see FIG. 12). Endoporter associated with Cas9/sgRNA complexes will be able to additionally bind aptamer DNA molecules to form a complex able to interact with the aptamer target on adipocyte cell surfaces, while preserving the cell uptake enhanced by Endoporter.

Alternatively, a second strategy is to covalently couple the aptamer to the Endo-Porter peptide creating a hybrid EP-aptamer molecule. Endo-Porter peptide is synthesized with an additional cysteine residue at either the N-terminus or C-terminus of the EP to introduce a thio group to the peptide. For non-cleavable linker conjugation, aptamer can be synthesized with a maleimide group at its 5' end. The maleimide group on the aptamer reacts with the thio group on the EP under pH 6.5-7.5 to form a stable non-cleavable thioether bond. This hybrid-aptamer molecule is incubated with Cas9/sgRNA complexes (see FIG. 12) to form the final aptamer-CriPs particles which are used for in vivo injections.

The CriPs/Aptamer complexes are tested in vitro on primary mouse adipocytes to ensure efficacy using T7E1 assay to quantify indel generation and immunoblotting to quantify expression of RIP140 protein.

Example 15

Identification of Alternative Therapeutic Target Genes for Type 2 Diabetes, Prediabetes and/or Gestation Diabetes Treatment A human clinical therapeutic tool to induce sustained "browning" in adipose tissue would greatly enhance treatment for subjects with type 2 diabetes, prediabetes and/or gestational diabetes. Thus, it is desirable to develop adipocyte-specific CriPs using a human cell system which will be more likely to translate to a safe and effective in vivo human therapeutic. Technology to isolate clonal precursors from human adipose tissue that can differentiate in vitro into "Beige" adipocytes with expression of UCP1 is utilized to identify new therapeutic targets for type 2 diabetes. High-throughput siRNA transfection and analysis of gene expression is used to identify loss-of function targets that result in enhanced UCP-1 expression in these cells.

Human subcutaneous adipose tissue is obtained from panniculectomies of post-bariatric surgery patients. Explants from human subcutaneous adipose tissue are cultured in EBM-2 medium supplemented with endothelial growth factors (EGM-2 MV) (Lonza) for 14 d. Single-cell suspensions from capillary growth (capillary network cells) are obtained using dispase, and these are plated on standard tissue culture plates. Adipogenic differentiation is induced by the replacement of EGM-2 MV with DMEM+10% FBS, 0.5 mM 3-isobutyl-1-methylxanthine, 1 µM dexamethasone and 1 µg/mL insulin (MDI). Seventy-two hours later, the differentiation medium is replaced by DMEM-FBS, which is replaced every 48 h until analysis. To obtain clonal populations, single-cell suspensions are obtained from capillary network cell cultures using trypsin, and then stained with 7-amino-actinomycin D (7-AAD) for live/dead cell identification, and sorted into individual wells of 384-well multi-well dishes by using a BSL3 BD FACSAria Cell Sorter (BD Biosciences). Clones are grown and expanded using EGM-2 MV. Viable clones are passaged onto 96-well multi-well dishes, which are differentiated as described above.

Cells are seeded into 384-well plates and differentiated by treatment with MDI medium as described. The human Ambion Silencer select library (Thermo-Fisher) consists of three independent siRNA targeting over 21,000 human gene sequences. This library is transfected into the cells using Endoporter as previously described (Tesz B J). After 72 hours cells are lysed and UCP1 mRNA levels assayed via the QuantiGene Singleplex HT Assay (Affymetrix) compared to 36B4 mRNA expression as an internal control. Top hits are considered as those that give >10-fold increase in UCP-1 expression AND are targeted by more than one of the three gene-specific siRNAs. Top hits are rescreened in a validation round and reproducible hits will be selected for further characterization.

Top siRNA hits are validated by siRNA transfection into human cells. Knockdown of the target gene is verified by RT-PCR and immunoblotting when possible. Change in expression of UCP1 and other thermogenic genes are also assessed. Verification of alterations in oxygen consumption and mitochondrial parameters expected from a thermogenic phenotype are assessed using Seahorse technology. Conversion to a brown or more thermogenic phenotype is signified by increased respiratory capacity, increased oxygen consumption, increased uncoupled respiration and increased fatty acid oxidation. Following transfection with targeting or non-specific control siRNAs, oxygen consumption and mitochondrial parameters in intact human cells is analyzed using the XF24 Extracellular Flux Analyzer, which is equipped with a FluxPak mini kit (#100867-100) from Seahorse Biosciences. In this system, oxygen consumption rates are calculated from four independent measurements obtained at 5-min intervals at baseline and after the automated addition of specific drugs. For each experiment, the means from three replicate wells are recorded. For the assessment of mitochondrial parameters, the values for the four independent measurements recorded for each condition are averaged, and parameters are calculated as follows using glucose as substrate: ATP-linked respiration=basal oxygen consumption rate (OCR)−oligomycin OCR; proton leak=oligomycin OCR−(rotenone+antimycin OCR); maximal capacity=FCCP OCR; reserve capacity=FCCP OCR− basal OCR; non-mitochondrial respiration=rotenone+antimycin OCR. Fatty acid oxidation is also assessed using palmitate as a substrate.

Top hits in this screen are further characterized by generating CriPs and aptamer-CriPs as described in Examples 1, 2, and 14. Assessment of CriPs and aptamer-CriPs-mediated gene deletion, implantation into immune deficient mice and metabolic improvement upon challenge with high fat diet-induced obesity and insulin resistance, are all performed as described in the examples above.

REFERENCES

Doench et al., "Optimized sgRNA design to maximize activity and minimize off-target effects of CRISPR-Cas9" Nat Biotech, 34: 184-191 (2016).

Puri et al., "RNAi-based gene silencing in primary mouse and human adipose tissues" J Lipid Res, 48: 465-72 (2007).

Steel et al., "Role of the RIP140 corepressor in ovulation and adipose biology" J Endocrinol, 185: 1-9 (2005).

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A composition comprising:
a nucleic acid-guided endonuclease,
a sequence-specific targeting nucleic acid, and
an amphipathic helical peptide,
wherein the nucleic acid-guided endonuclease, the sequence-specific targeting nucleic acid and the amphipathic helical peptide form a complex,
wherein the amphipathic helical peptide mediates delivery of the complex to a target cell, and wherein the nucleic acid-guided endonuclease mediates editing or deletion of a target gene in the target cell,
wherein the sequence-specific targeting nucleic acid is a guide RNA, and
wherein the guide RNA comprises a region having at least 90% sequence identity with the sequence of SEQ ID NO: 1, SEQ ID NO: 2, SEQ ID NO: 3, or SEQ ID NO: 4.

2. The composition of claim 1, wherein the amphipathic helical peptide is selected from the group consisting of:

H2N-LHHLLHHLLHHLHHLLHHLHHLLHHL-COOH;

H2N-LHKLLHHLLHHLHKLLHHLHHLLHKL-COOH;

H2N-LHKLLHHLLHKLHHLLHKLHHLLHHL-COOH;

H2N-LHHLLHHLLHHLHHL-COOH;

H2N-HHLLHHLHHLLHHL-COOH;

H2N-LHLLHHLLHHLHHL-COOH;

H2N-LHHLLHLLHHLLHHL-COOH;

H2N-LHKLLHHLLHHLHK-COOH;

H2N-LHKLLHHLHHLLHKL-COOH;

H2N-KLHHLLHKLHHLLHH-COOH;

H2N-HLHLLHHLLHH-COOH;

H2N-LHLLHHLLHH-COOH;

H2N-LHKLLHHLLHKLHHL-COOH;

H2N-LHLLHH-COOH;

H2N-LHHLL-COOH;

H2N-LHKLL-COOH
and

Endo-Porter.

3. The composition of claim 1, wherein the nucleic acid-guided endonuclease is Cas9.

4. The composition of claim 3, wherein the Cas9 is an *E. coli* Cas9.

5. The composition of claim 3, wherein the Cas9 is a *Streptococcus pyogenes* Cas9.

6. The composition of claim 3, wherein the Cas9 is a *Staphylococcus aureus* Cas9.

7. The composition of claim 1, wherein the complex further comprises an aptamer molecule with binding specificity for the target cell.

8. The composition of claim 7, wherein the aptamer forms a non-covalent binding interaction with the amphipathic helical peptide.

9. The composition of claim 7, wherein the aptamer is conjugated to the amphipathic helical peptide.

10. The composition of claim 1, wherein the guide RNA comprises a region having at least 95% sequence identity with the sequence of SEQ ID NO: 1, SEQ ID NO: 2, SEQ ID NO: 3, or SEQ ID NO: 4.

11. The composition of claim 1, wherein the guide RNA comprises the sequence of SEQ ID NO: 1, SEQ ID NO: 2, SEQ ID NO: 3, or SEQ ID NO: 4.

12. The composition of claim 1, wherein the target cell is mammalian.

13. The composition of claim 12, wherein the target cell is an adipocyte or a pre-adipocyte.

14. The composition of claim 13, wherein the complex is encapsulated in a glucan particle (GP).

15. A guide RNA, wherein the guide RNA comprises a region having at least 90% sequence identity with the sequence of SEQ ID NO: 1, SEQ ID NO: 2, SEQ ID NO: 3, or SEQ ID NO: 4.

* * * * *

SEQUENCE LISTING

```
<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtttggagt cacgtcaggg                                                   20

<210> SEQ ID NO 2
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 2
ggatttaagg tgctatggcg                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggagtcgaag aacatctgca                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggagtactgc aggcatacgg                                              20

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu His His Leu Leu His His Leu Leu His His Leu His His Leu Leu
1               5                   10                  15

His His Leu His His Leu Leu His His Leu
            20                  25

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu His Lys Leu Leu His His Leu Leu His His Leu His Lys Leu Leu
1               5                   10                  15

His His Leu His His Leu Leu His Lys Leu
            20                  25

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu His Lys Leu Leu His His Leu Leu His Lys Leu His His Leu Leu

```
                1               5                  10                  15
His Lys Leu His His Leu Leu His His Leu
            20                  25

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu His His Leu Leu His His Leu Leu His His Leu His His Leu
1               5                  10                  15

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His His Leu Leu His His Leu His His Leu Leu His His Leu
1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu His Leu Leu His His Leu Leu His His Leu His His Leu
1               5                  10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu His His Leu Leu His Leu Leu His His Leu Leu His Leu
1               5                  10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu His Lys Leu Leu His His Leu Leu His His Leu His Lys
1               5                  10

<210> SEQ ID NO 13
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Leu His Lys Leu Leu His His Leu His His Leu Leu His Lys Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Leu His His Leu Leu His Lys Leu His Leu Leu His His
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Leu His Leu Leu His His Leu Leu His His
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu His Leu Leu His His Leu Leu His His
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu His Lys Leu Leu His His Leu Leu His Lys Leu His His Leu
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu His Leu Leu His His
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu His His Leu Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu His Lys Leu Leu
1               5

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21 guuuuguac ucucaagauu ua                                              22

<210> SEQ ID NO 22
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22 guuuuguac ucuca                                                      15

<210> SEQ ID NO 23
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
guuuuagagc ua                                                        12

<210> SEQ ID NO 24
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
```

-continued

```
guuuuagagc uag                                                    13

<210> SEQ ID NO 25
<211> LENGTH: 60
<212> TYPE: RNA
<213> ORGANISM: Streptococcus pyogenes

<400> SEQUENCE: 25
uagcaaguua aaauaaggcu aguccguuau caacuugaaa aaguggcacc gagucggugc    60

<210> SEQ ID NO 26
<211> LENGTH: 45
<212> TYPE: RNA
<213> ORGANISM: Streptococcus pyogenes

<400> SEQUENCE: 26
uagcaaguua aaauaaggcu aguccguuau caacuugaaa aagug                    45

<210> SEQ ID NO 27
<211> LENGTH: 32
<212> TYPE: RNA
<213> ORGANISM: Streptococcus pyogenes

<400> SEQUENCE: 27
uagcaaguua aaauaaggcu aguccguuau ca                                  32

<210> SEQ ID NO 28
<211> LENGTH: 85
<212> TYPE: RNA
<213> ORGANISM: Streptococcus thermophilus

<400> SEQUENCE: 28
uaaaucuugc agaagcuaca aagauaaggc uucaugccga aaucaacacc cugucauuuu    60
auggcagggu guuucguua uuuaa                                           85

<210> SEQ ID NO 29
<211> LENGTH: 77
<212> TYPE: RNA
<213> ORGANISM: Streptococcus thermophilus

<400> SEQUENCE: 29
ugcagaagcu acaaagauaa ggcuucaugc cgaaaucaac acccugucau uuuauggcag    60
gguguuuucg uuauuua                                                   77

<210> SEQ ID NO 30
<211> LENGTH: 65
<212> TYPE: RNA
<213> ORGANISM: Streptococcus thermophilus

<400> SEQUENCE: 30
ugcagaagcu acaaagauaa ggcuucaugc cgaaaucaac acccugucau uuuauggcag    60
ggugu                                                                65

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
```
gggcgaggag ctgttcaccg                                               20

<210> SEQ ID NO 32
<211> LENGTH: 5
<212> TYPE: PRT
<213> ORGANISM: Unknown
<220> FEATURE:
<223> OTHER INFORMATION: Description of Unknown:
      CTBP motif sequence
<220> FEATURE:
<221> NAME/KEY: MOD_RES
<222> LOCATION: (2)..(2)
<223> OTHER INFORMATION: Any amino acid

<400> SEQUENCE: 32

Pro Xaa Asp Leu Ser
1               5

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggagtcgaag aacatctgca tgg                                           23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggagtcgaag aacatctgca tgg                                           23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggactataag aacatctgca tgg                                           23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggagatgaag aacatgtgca tgg                                           23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
ggagaagaag aacctctgca tgg                                          23

<210> SEQ ID NO 38
<211> LENGTH: 45
<212> TYPE: DNA
<213> ORGANISM: Mus sp.

<400> SEQUENCE: 38
ggtgagcaag ggcgaggagc tgttcaccgg ggtggtgccc atcct                  45

<210> SEQ ID NO 39
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggtgagcaag ggcgaggagc tgttcaaccg gggtggtgcc catcct                 46

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggtgagcaag ggcgacaccg gggtggtgcc catcct                            36

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggtgagcaag ggcgagcggg gtggtgccca tcct                              34

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ggtgagcaag ggcgaggagc tggggtggtg cccatcct                          38

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggtgagcaag ggcgaggagc cggggtggtg cccatcct        38

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggtgagcaag ggcgaggagc tgaccggggt ggtgcccatc ct        42

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggtgagcaag ggcgaggagc tgttaccggg gtggtgccca tcct        44

<210> SEQ ID NO 46
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggtgagcaag ggcgaggagc tgttccgggg tggtgcccat cct        43

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ggtgagcaag ggcgaggagc taccggggtg gtgcccatcc t        41

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtgagcaag ggcgaggagc tgttggggtg gtgcccatcc t        41

```
<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggtgagcaag ggcgaggagc tggtgcccat cct                                      33
```